(12) United States Patent
Lind et al.

(10) Patent No.: US 9,642,637 B1
(45) Date of Patent: May 9, 2017

(54) STONE RETRIEVER FOR FLEXIBLE ENDOSCOPES HAVING SMALL DIAMETER WORKING CHANNELS

(71) Applicant: Annex Medical, Inc., Minnetonka, MN (US)

(72) Inventors: Stuart Lind, Edina, MN (US); Daniel L. Dostal, Eden Prairie, MN (US); Eugene C. Karels, Minnetonka, MN (US)

(73) Assignee: Annex Medical, Inc., Minnetonka, MN (US)

( * ) Notice: Subject to any disclaimer, the term of this patent is extended or adjusted under 35 U.S.C. 154(b) by 0 days.

(21) Appl. No.: 13/987,137

(22) Filed: Jul. 2, 2013

Related U.S. Application Data

(63) Continuation of application No. 11/094,894, filed on Mar. 31, 2005, now Pat. No. 8,523,879.

(51) Int. Cl.
*A61B 17/221* (2006.01)

(52) U.S. Cl.
CPC .................. *A61B 17/221* (2013.01)

(58) Field of Classification Search
CPC .......... A61B 17/221; A61B 2017/2212; A61B 2017/2215
USPC ........ 606/110–114, 127, 128, 159, 180, 198, 606/200, 213; 600/201
See application file for complete search history.

(56) References Cited

U.S. PATENT DOCUMENTS

| 651,395 | A | 6/1900 | Strapp |
| 1,054,960 | A | 3/1913 | Butner |
| 1,677,671 | A | 7/1928 | Councill |
| 2,054,149 | A | 9/1936 | Frederick |
| 2,918,919 | A | 12/1959 | Wallace |
| 2,943,626 | A | 7/1960 | Dormia |
| 3,008,467 | A | 11/1961 | Morris |
| 3,080,867 | A | 3/1963 | Eichinger |
| 3,162,214 | A | 12/1964 | Bazinet |
| 3,674,014 | A | 7/1972 | Tillander |
| 3,791,387 | A | 2/1974 | Itoh |
| 3,828,790 | A | 8/1974 | Curtiss et al. |
| 3,903,892 | A | 9/1975 | Komiya |
| 3,955,578 | A | 5/1976 | Chamness et al. |

(Continued)

OTHER PUBLICATIONS

Application and File history for U.S. Appl. No. 11/094,894, filed Mar. 31, 2005, issued as U.S. Pat. No. 8,523,879 on Sep. 3, 2013. Inventors: Lind et al.

(Continued)

*Primary Examiner* — Dianne Dornbusch
(74) *Attorney, Agent, or Firm* — Patterson Thuente Pedersen, P.A.

(57) ABSTRACT

A medical retrieval device and method used in endoscopic procedures to retrieve stones has a shaft comprising a sheath with a lumen and a drive wire slidably disposed within the lumen for operating a stone entrapping mechanism on the distal end of the retrieval device. The shaft, sheath and drive wire each have proximal, intermediate and distal portions, and each of the corresponding portions are in generally similar locations along the longitudinal length of the device. The stone entrapping mechanism is constructed of a plurality of flexible elements that are outwardly disposed to form an entrapment space and having an open and closed configuration. Configuration of the flexible elements and the entrapment space vary within the stone entrapment mechanism.

24 Claims, 16 Drawing Sheets

(56) References Cited

U.S. PATENT DOCUMENTS

| | | |
|---|---|---|
| 4,046,149 A | 9/1977 | Komiya |
| 4,046,150 A | 9/1977 | Schwartz et al. |
| 4,198,960 A | 4/1980 | Utsugi |
| 4,299,225 A | 11/1981 | Glassman |
| 4,347,846 A | 9/1982 | Dormia |
| 4,590,938 A | 5/1986 | Segura et al. |
| 4,611,594 A | 9/1986 | Grayhack et al. |
| 4,612,931 A | 9/1986 | Dormia |
| 4,625,726 A | 12/1986 | Duthoy |
| 4,633,871 A | 1/1987 | Shinozuka |
| 4,655,219 A | 4/1987 | Petruzzi |
| 4,685,895 A | 8/1987 | Hatten |
| 4,691,705 A | 9/1987 | Okada |
| 4,790,812 A | 12/1988 | Hawkins, Jr. et al. |
| 4,802,461 A | 2/1989 | Cho |
| 4,807,626 A | 2/1989 | McGirr |
| 4,815,476 A | 3/1989 | Clossick |
| 4,927,426 A | 5/1990 | Dretler |
| 4,955,384 A | 9/1990 | Taylor et al. |
| 4,994,079 A | 2/1991 | Genese et al. |
| 5,010,894 A | 4/1991 | Edhag |
| 5,057,114 A | 10/1991 | Wittich et al. |
| 5,064,428 A | 11/1991 | Cope et al. |
| 5,066,295 A | 11/1991 | Kozak et al. |
| 5,083,549 A | 1/1992 | Cho et al. |
| 5,098,441 A | 3/1992 | Wechler |
| 5,146,928 A | 9/1992 | Esser |
| 5,176,688 A | 1/1993 | Narayan et al. |
| 5,201,741 A | 4/1993 | Dulebohn |
| 5,325,845 A | 7/1994 | Adair |
| 5,330,482 A | 7/1994 | Gibbs et al. |
| 5,376,094 A | 12/1994 | Kline |
| 5,381,782 A | 1/1995 | DeLaRama et al. |
| 5,411,025 A | 5/1995 | Webster |
| 5,484,384 A | 1/1996 | Fearnot |
| 5,496,330 A | 3/1996 | Bates et al. |
| 5,499,981 A | 3/1996 | Kordis |
| 5,549,661 A | 8/1996 | Kordis |
| 5,573,520 A | 11/1996 | Schwartz et al. |
| 5,573,530 A | 11/1996 | Fleury et al. |
| 5,595,186 A | 1/1997 | Rubinstein et al. |
| 5,647,870 A | 7/1997 | Kordis et al. |
| 5,681,263 A | 10/1997 | Flesch |
| 5,718,714 A | 2/1998 | Livneh |
| 5,722,423 A | 3/1998 | Lind et al. |
| 5,788,710 A | 8/1998 | Bates et al. |
| 5,792,145 A | 8/1998 | Bates et al. |
| 5,817,104 A | 10/1998 | Bilitz et al. |
| 5,820,630 A | 10/1998 | Lind |
| 5,833,632 A | 11/1998 | Jacobsen et al. |
| 5,891,017 A | 4/1999 | Swindle et al. |
| 5,911,739 A | 6/1999 | Kordis et al. |
| 5,922,443 A | 7/1999 | Larsen et al. |
| 5,931,830 A | 8/1999 | Jacobsen et al. |
| 5,944,728 A | 8/1999 | Bates |
| 5,957,932 A | 9/1999 | Bates et al. |
| 5,989,266 A | 11/1999 | Foster |
| 6,013,086 A | 1/2000 | Ouchi |
| 6,015,415 A | 1/2000 | Avellanet |
| 6,053,934 A | 4/2000 | Andrews et al. |
| 6,090,129 A | 7/2000 | Ouchi |
| 6,093,196 A | 7/2000 | Okada |
| 6,096,053 A | 8/2000 | Bates |
| 6,152,932 A | 11/2000 | Ternstrom |
| 6,159,220 A | 12/2000 | Gobron et al. |
| 6,168,603 B1 | 1/2001 | Leslie et al. |
| 6,183,482 B1 | 2/2001 | Bates et al. |
| 6,190,394 B1 | 2/2001 | Lind et al. |
| 6,203,552 B1 | 3/2001 | Bagley et al. |
| 6,216,044 B1 | 4/2001 | Kordis |
| 6,224,612 B1 | 5/2001 | Bates et al. |
| 6,235,026 B1 | 5/2001 | Smith |
| 6,258,101 B1 | 7/2001 | Blake, III |
| 6,273,876 B1 | 8/2001 | Klima et al. |
| 6,280,451 B1 | 8/2001 | Bates et al. |
| 6,299,612 B1 | 10/2001 | Ouchi |
| 6,302,895 B1 | 10/2001 | Gobron |
| 6,325,807 B1 | 12/2001 | Que |
| 6,348,056 B1 | 2/2002 | Bates et al. |
| 6,350,266 B1 | 2/2002 | White et al. |
| 6,352,539 B1 | 3/2002 | Avellanet |
| D457,955 S | 5/2002 | Bilitz |
| 6,398,791 B1 | 6/2002 | Que et al. |
| 6,419,679 B1 | 7/2002 | Dhindsa |
| 6,458,145 B1 | 10/2002 | Ravenscroft |
| 6,494,885 B1 | 12/2002 | Dhindsa |
| 6,500,182 B2 | 12/2002 | Foster |
| 6,527,781 B2 | 3/2003 | Bates et al. |
| 6,551,327 B1 | 4/2003 | Dhindsa |
| 6,575,970 B2 | 6/2003 | Quick |
| 6,585,734 B2 | 7/2003 | Levinson |
| 6,626,915 B2 | 9/2003 | Leveillee |
| 6,652,537 B2 | 11/2003 | Mercereau |
| 6,676,668 B2 | 1/2004 | Mercereau et al. |
| 6,682,493 B2 | 1/2004 | Mirigian |
| 6,695,834 B2 | 2/2004 | Gellman et al. |
| 6,740,030 B2 | 5/2004 | Martone et al. |
| 6,743,237 B2 | 6/2004 | Dhindsa |
| 6,752,811 B2 | 6/2004 | Chu et al. |
| 6,921,397 B2 | 7/2005 | Corcoran et al. |
| 7,101,379 B2 | 9/2006 | Gregory, Jr et al. |
| 7,413,563 B2 | 8/2008 | Corcoran et al. |
| 7,559,934 B2 | 7/2009 | Teague |
| 8,021,372 B2 | 9/2011 | Bilitz |
| 8,523,879 B1 | 9/2013 | Lind et al. |
| 8,617,177 B2 | 12/2013 | Uihlein |
| 8,870,895 B2 | 10/2014 | Bilitz |
| 9,101,383 B1 | 8/2015 | Dostal et al. |
| 2001/0001315 A1 | 5/2001 | Bates et al. |
| 2002/0026202 A1 | 2/2002 | Honey et al. |
| 2002/0068954 A1 | 6/2002 | Foster |
| 2002/0091394 A1 | 7/2002 | Reynolds |
| 2002/0133170 A1 | 9/2002 | Tsuruta |
| 2002/0133171 A1 | 9/2002 | Que et al. |
| 2003/0009176 A1 | 1/2003 | Bilitz |
| 2003/0023247 A1 | 1/2003 | Lind et al. |
| 2003/0055401 A1 | 3/2003 | Larson et al. |
| 2003/0055423 A1 | 3/2003 | Levinson |
| 2003/0078593 A1 | 4/2003 | Bates et al. |
| 2003/0088254 A1 | 5/2003 | Gregory, Jr. et al. |
| 2003/0105480 A1 | 6/2003 | Wiener et al. |
| 2003/0105488 A1 | 6/2003 | Chu |
| 2003/0109888 A1 | 6/2003 | Mercereau |
| 2003/0109889 A1 | 6/2003 | Mercereau |
| 2003/0120281 A1 | 6/2003 | Bates et al. |
| 2003/0139750 A1 | 7/2003 | Shinozuka et al. |
| 2003/0176859 A1 | 9/2003 | Levinson |
| 2003/0225419 A1 | 12/2003 | Lippitt et al. |
| 2004/0106852 A1 | 6/2004 | Windheuser et al. |
| 2004/0122444 A1 | 6/2004 | Gerard |
| 2004/0133213 A1 | 7/2004 | Bagley et al. |
| 2004/0199048 A1 | 10/2004 | Clayman et al. |
| 2004/0199200 A1 | 10/2004 | Teague |
| 2004/0215212 A1 | 10/2004 | Teague et al. |
| 2005/0080400 A1 | 4/2005 | Corcoran et al. |
| 2005/0125016 A1 | 6/2005 | Trerotola |
| 2012/0095477 A1 | 4/2012 | Bilitz |

OTHER PUBLICATIONS

Application and File history for U.S. Appl. No. 10/190,218, filed Jul. 5, 2002 issued as U.S. Pat. No. 8,021,372 on Sep. 20, 2011. Inventors: Bilitz.

Application and File history for U.S. Appl. No. 13/236,031, filed Sep. 19, 2011, issued as U.S. Pat. No. 8,870,895 on Oct. 28, 2014. Inventor: Bilitz.

Application and File history for U.S. Appl. No. 12/821,792, filed Jun. 23, 2010, issued as U.S. Pat. No. 9,101,383 on Aug. 11, 2015. Inventors: Dostal et al.

Application and File history for U.S. Appl. No. 10/189,858, filed Jul. 3, 2002. Inventors: Lind et al.

Monga et al., Systemic evaluation of stone basket dimensions, Urology, 63 (6), 2004.

(56) References Cited

OTHER PUBLICATIONS

Landman et al., Bare baked baskets: ureteroscope deflection and flow characteristics with intact and disassembled ureteroscopic nitinol stone baskets , Journal of Urology, vol. 167 2377-2379, Jun. 2002.

Bhayani et al., Bare naked baskets: optimizing ureteroscopic stone extraction, Urology 60 (1), 2002.

Afane et al., Flexible ureteroscopes: a single center evaluation of the durability and function of the new endoscopes smaller than 9fr, Journal of Urology, vol. 164 1164-1168, Oct. 2000.

Parkin et al., Flexible ureteroscopes: a users guide, BJU International, (2002), 90, 640-643.

Chiu et al., Comparison of the mechanical, flow and optical properties of contemporary flexible ureteroscopes, Urology 62 (5), 2003.

Pasqui et al., Impact on active scope deflection and irrigation flow of all endoscopic working tools during flexible ureteroscopy, European Urology 45 (2004) 58-64.

Images displayed at American Urological Association trade show in Chicago, IL on Apr. 27, 2003. 5 pages.

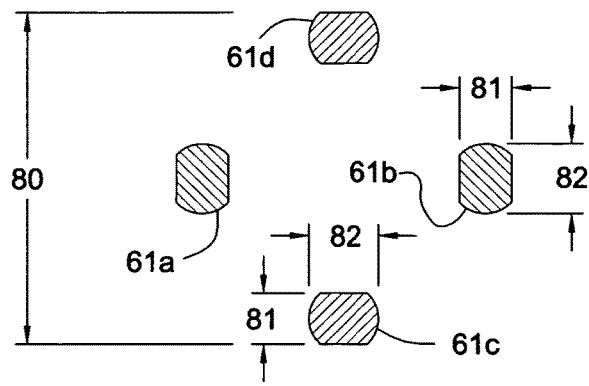
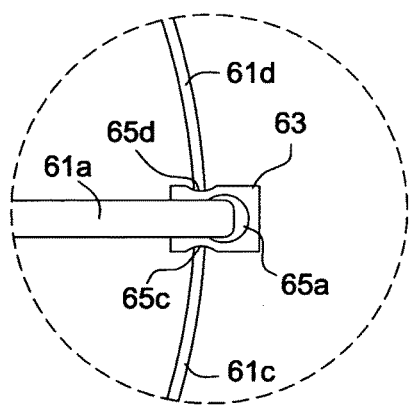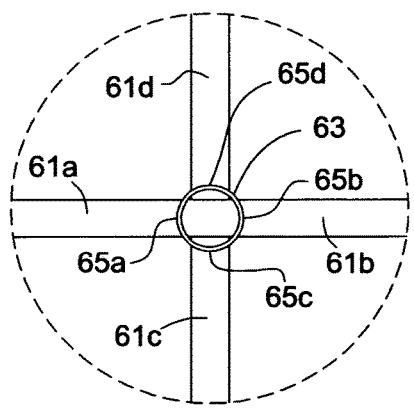
Fig.3a
Fig.3b          Fig.3c

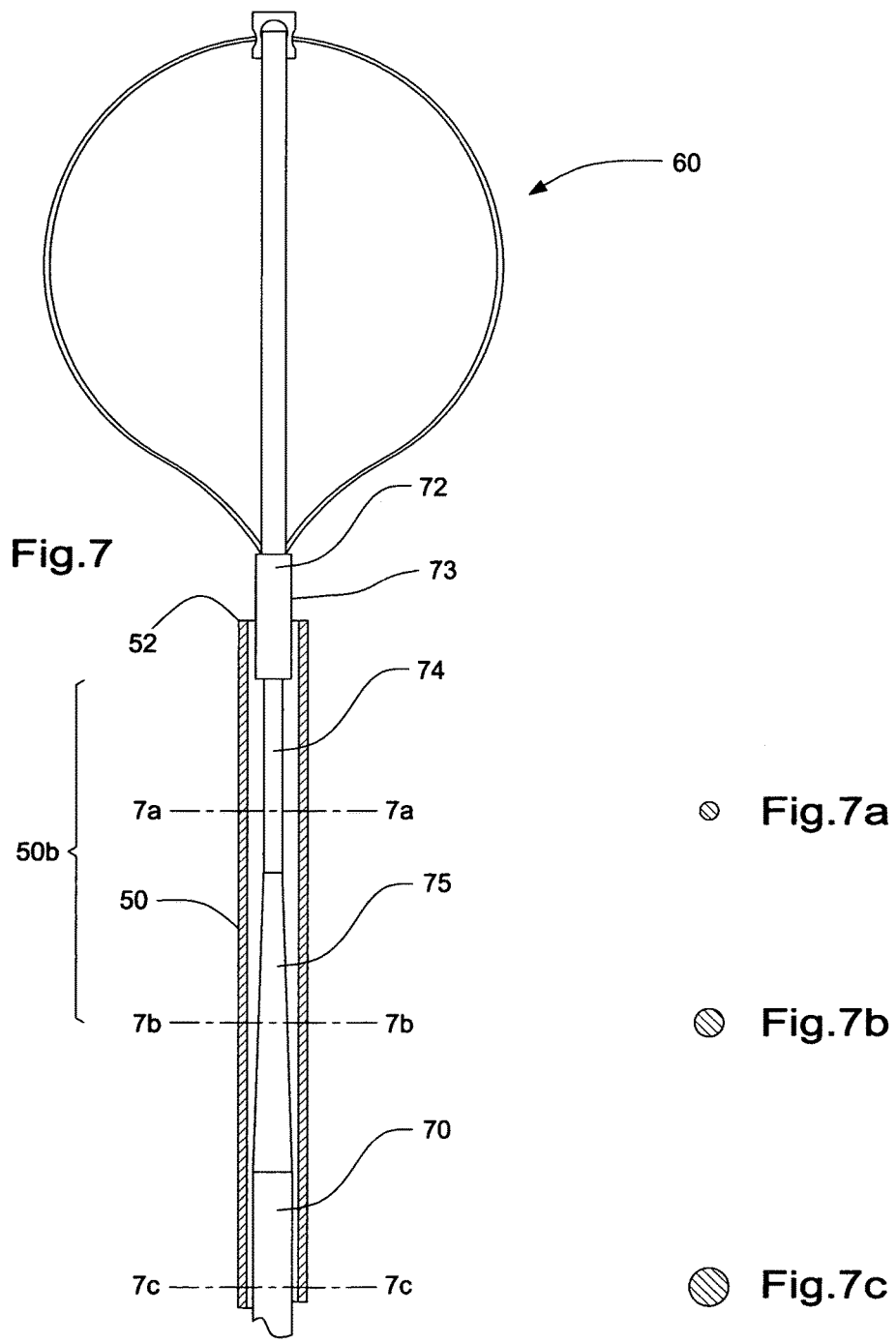

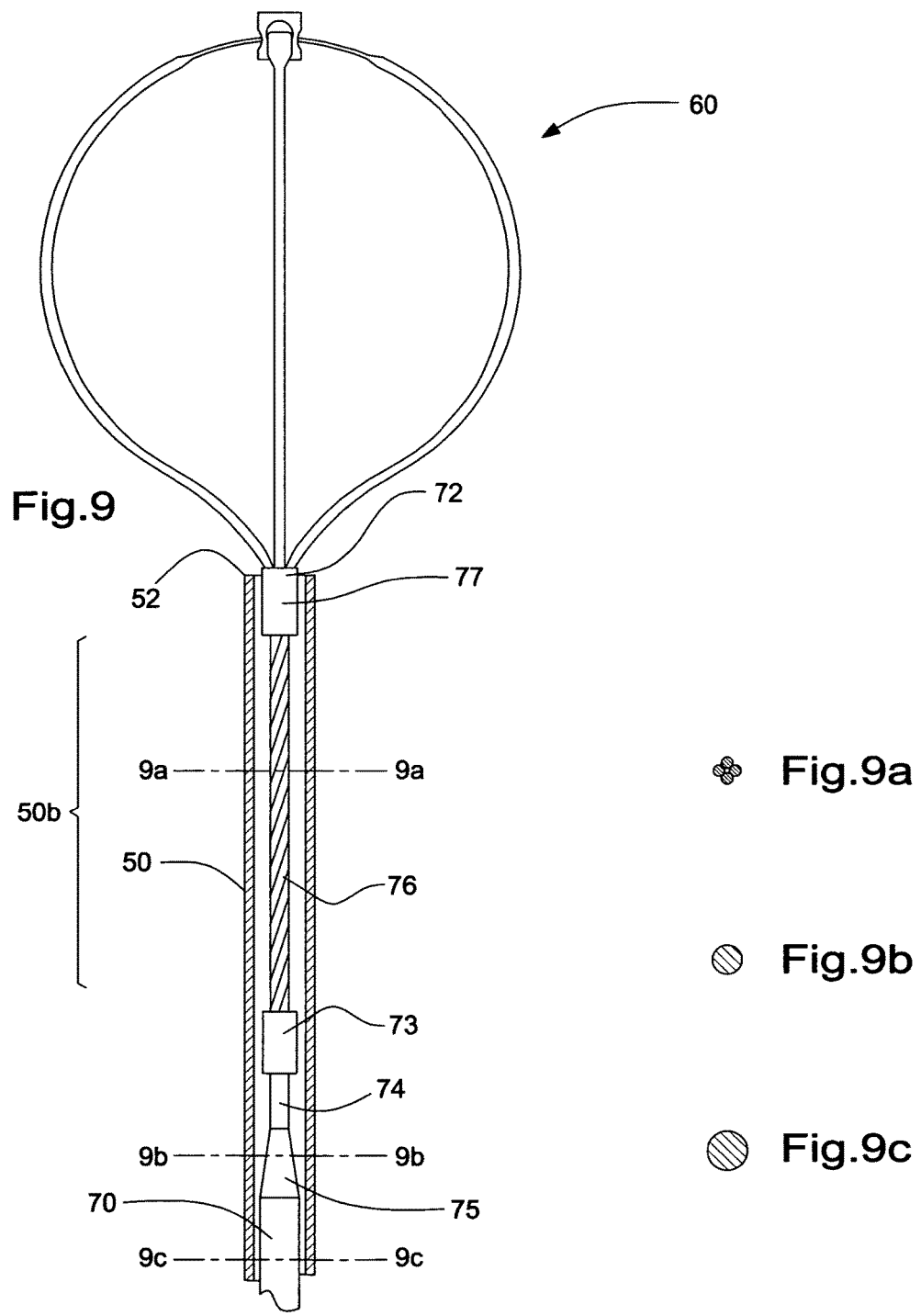

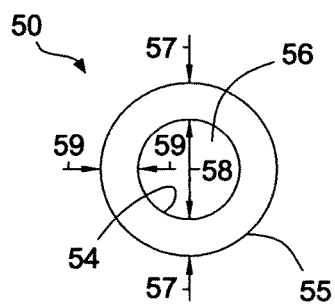
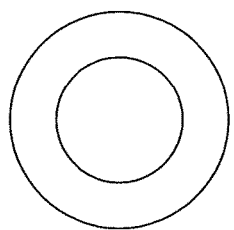
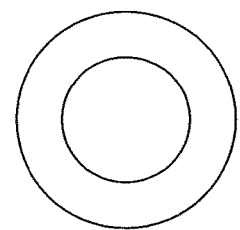
Fig. 10a Fig. 10b Fig. 10c
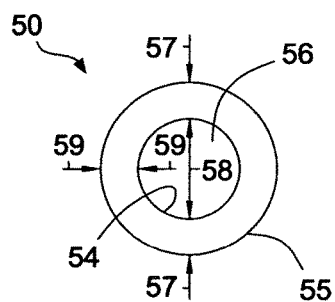
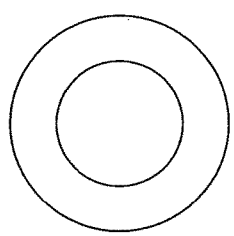
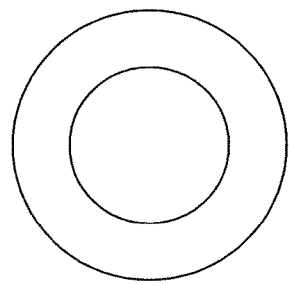
Fig. 11a Fig. 11b Fig. 11c
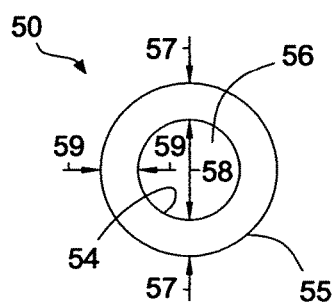
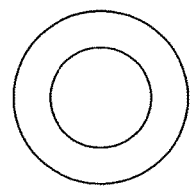
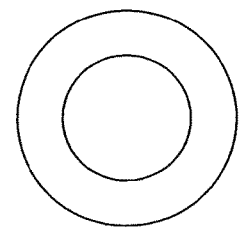
Fig. 12a Fig. 12b Fig. 12c

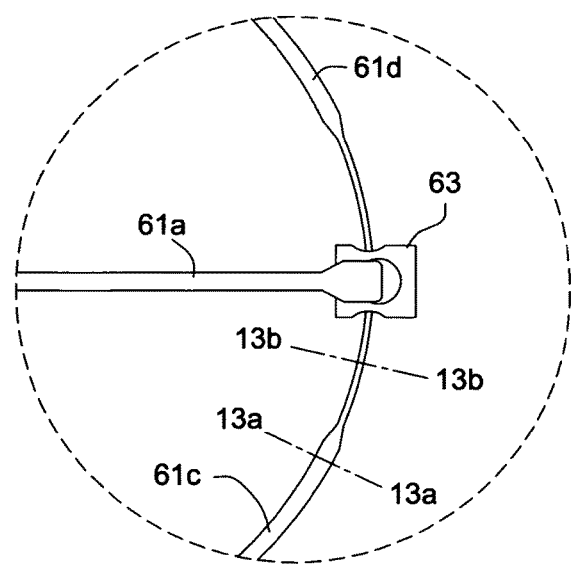
Fig.13
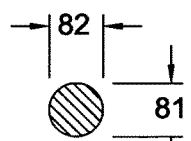
Fig.13a₁
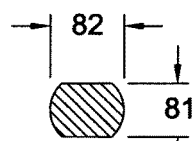
Fig.13a₂
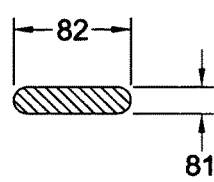
Fig.13b₁
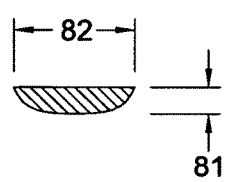
Fig.13b₂
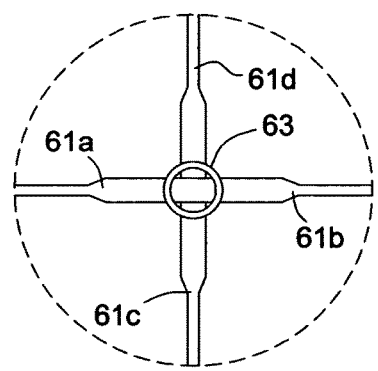
Fig.14

FLEXIBLE URETEROSCOPES SMALLER THAN 9Fr.

| Manufacturer<br>Model# | Storz<br>11274AA | ACMI<br>AUR-7 | Wolf<br>735.172 | Olympus<br>URF/P3 |
|---|---|---|---|---|
| Length (mm) | | | | |
|   Total | 990 | 1000 | 940 | 1010 |
|   Shaft Only | 700 | 650 | 700 | 700 |
| Shaft O.D. (Fr) | | | | |
|   Distal Portion | 7.5 | 7.2-7.4 | 7.0 | 8.1 |
|   Proximal Portion | 8.7 | 7.4-9.5 | 8.0-9.0 | 8.4 |
| Working Channel I.D. (Fr) | 3.6 | 3.6 | 3.6 | 3.6 |

References

1. Afane, J. et al: Flexible Ureteroscopes: A single center evaluation of durability and function of the new endoscopes smaller than 9Fr., Journal of Urology, Vol. 164, 1164-1168, October 2000.

Fig.16

3.6Fr. ID x 80cm LONG WORKING CHANNEL IRRIGATION FLOW TEST RESULTS

| DESCRIPTION | BASKET SHAFT ONLY | SHAFT AND LASER FIBER [4] |
|---|---|---|
| PRIOR ART 3.0 Fr. TIPLESS [2] | 0.6 ml/min | N/A [3] |
| PRIOR ART 2.4 Fr. TIPLESS [2] | 3.5 ml/min | N/A [3] |
| PRIOR ART 1.9 Fr. TIPLESS [2] | 8.3 ml/min | 4.6 ml/min |
| PRESENT INVENTION 1.83 Fr. | 10.1 ml/min | 5.5 ml/min |
| PRESENT INVENTION 1.71 Fr. | 12.1 ml/min | 5.8 ml/min |
| PRESENT INVENTION 1.60 Fr. | 13.6 ml/min | 6.4 ml/min |
| PRESENT INVENTION 1.52 Fr. | 15.2 ml/min | 7.9 ml/min |

Notes:

1. Empty channel flow rate = 45.4 ml/min.

2. Boston Scientific Stone Baskets: 3.0 Fr.(p/n 390-103), 2.4 Fr.(p/n 390-101), 1.9 Fr.(p/n 390-105).

3. Data not available because the stone basket shaft and laser fiber will not fit together in the channel.

4. Laser fiber from Laser Peripherals LLC, Model# HBLF-200, (outer diameter = 400μm).

Fig.20

STONE RETRIEVER FOR FLEXIBLE ENDOSCOPES HAVING SMALL DIAMETER WORKING CHANNELS

This application is a continuation of U.S. application Ser. No. 11/094,894 filed Mar. 31, 2005, now issued as U.S. Pat. No. 8,523,879, which is hereby fully incorporated by reference.

FIELD OF THE INVENTION

The present invention relates generally to medical devices with means for concretion removal. More particularly, the present invention relates to stone retrievers for use with flexible endoscopes having small diameter working channels.

BACKGROUND OF THE INVENTION

Medical instruments are currently in use that reduce the invasiveness and potential trauma previously associated with various medical procedures. One such procedure is the removal from the body of naturally occurring non-tissue objects referred to as stones, such as kidney stones and gallstones. Various medical retrieval devices are available which allow these stone-type objects to be removed from the body, for example via the urinary tract, without requiring major surgery. Typically, such instruments consist of two or more flexible elements. The flexible elements, such as wires, are formed in the shape of a resiliently collapsible basket, cage, grasper, or other entrapping mechanism. This basket is attached to a drive wire or actuation cable that passes through the lumen of a flexible sheath, which typically has an outer diameter of 1.9 to 3.0 Fr (1 Fr=0.33 mm) and is usually greater than 50 cm in length. The sheath and drive wire comprise the shaft portion of the device. At the proximal end of the shaft, the sheath and drive wire are attached to a multi-part handle, normally constructed of thermoplastic materials, which can typically be operated by the user with a single hand.

By manipulating the handle, the drive wire can be pulled back relative to the sheath, collapsing the basket as it retracts into the sheath. In this closed position, the sheath can be passed through the working channel of an endoscope to the proximity of the stone to be removed within the patient's body. By again manipulating the handle, which remains outside the endoscope and the patient's body, the basket is deployed from the end of the sheath, and expands to its open position. The device is then manipulated using the handle until the stone becomes enclosed within the basket. This manipulation may include advancing, withdrawing and/or rotating the basket in order to get the stone to pass between the flexible elements that comprise the basket. When the stone has been successfully engaged within the basket, the basket is partially closed to secure the stone within the basket wires, and the endoscope and the retrieval device containing the stone are then simultaneously removed from the body.

Many different basket configurations are in use for endoscopic object removal procedures. One conventional basket configuration uses a small diameter tube, typically 0.1 to 0.2 inches long, that extends beyond the distal end of the basket and inside of which the basket wires are joined at their distal end. Examples of such an extending tip basket configuration are shown in U.S. Patent Publ. No. 2003/0078593, and U.S. Pat. Nos. 4,927,426, 5,496,330, 6,168,603, and 6,190,394. Unfortunately, an extending basket tip has the disadvantage that the extending tip can cause trauma to body tissue, resulting in patient discomfort and bleeding, which not only may be injurious, but may also blur the physician's field of vision, thereby making the procedure more difficult or impossible. The extending tip is also a design disadvantage in many stone capture attempts (such as stone located in a calyx of the kidney) because the extended tip encounters structures so that the basket wires are hindered or prohibited from reaching the distal side of the stone.

The problems with extending tip designs for baskets have been addressed by baskets that are substantially tipless. Several types of tipless basket designs are known in the art as described, for example, in U.S. Pat. Nos. 4,590,938, 5,057,114, 5,989,266, 6,159,220, 6,224,612, 6,527,781, and 6,626,915, U.S. Patent Publ. Nos. 2003/0088254 and 2004/0133213 and U.S. patent application Ser. No. 10/831,267. These tipless baskets generally consist of multiple wire loops arranged in a manner similar to an eggwhip. The wire loops may or may not be connected at the basket's distal end, but the manner of connection is such that there is no substantial extending tip.

Tipless baskets are capable of retrieving stone-like objects, such as kidney stones, from difficult to access locations, such as the calices of the kidney. In order to access the kidney, a flexible endoscope, such as a flexible ureteroscope, is normally required. Flexible ureteroscopes are equipped with a mechanism for actively deflecting the tip of the ureteroscope in order to access locations that cannot be reached with a head-on approach, such as the upper and lower pole calices of the kidney. Typical flexible ureteroscopes can deflect up to about 180 degrees. Flexible ureteroscopes normally have one working channel, about 3.6 Fr in diameter, which is used for both irrigation fluid and working instruments, such as stone retrieval and lithotripsy devices. Irrigation is used to maintain clear visibility in the field of view, distend surrounding tissue to create an open working field, and to flush away small stone fragments resulting from lithotripsy procedures. Even with atraumatic tipless baskets, some bleeding often results from the manipulation of stones, particularly when the stone is impacted in the surrounding tissue. Small amounts of blood, when mixed with the saline used for irrigation, can significantly obscure the field of view.

During the course of a urological retrieval procedure, large stones are often fragmented using a lithotripsy device such as a laser. The laser fiber is passed through the working channel of the scope to the location of the stone in a similar manner to the retrieval device, and delivers laser energy to fragment the stone. One way that such a procedure is performed is that a tipless basket is first used to capture a stone located in a difficult to reach location (such as a lower pole calyx of the kidney) and then release the stone in a more accessible location for lithotripsy. The basket is then removed from the endoscope and replaced with the laser fiber, which is used to fragment the stone. The laser fiber is then withdrawn, and the tipless basket returned to the working channel of the scope to remove the larger fragments.

U.S. Pat. Nos. 6,325,807 and 6,398,791 disclose retrieval devices with an intermediate portion of the sheath near the distal end being more flexible than the rest of the sheath. This is accomplished by using several layers of different materials to construct the sheath. These prior art sheaths constructed of several layers of different materials are not practical for very small diameter sheaths, such as less than 1.7 Fr, because of the greater sheath wall thickness needed for the multiple layers. Additionally, the flexible portion of the sheath weakens the column strength of the sheath. This can make insertion of the device into the working channel of the ureteroscope through an endoscopic seal or adapter more difficult, and often requires a separate introducer to make the insertion possible. The weaker flexible portion of the sheath also is more susceptible to kinking or other damage that could result in a reduction in device functionality.

U.S. Patent Publ. No. 2004/0199048 discloses several designs intended to improve fluid flow in a working channel of a ureteroscope. One design is a basket without a sheath, where the basket is closed by withdrawing into the endoscope working channel. A second design is a basket with a ribbed or slotted sheath to increase fluid flow. A third design is to replace the sheath with a single thin control rod attached to a collar at the distal end for retracting the basket. A fourth design has a tapered sheath that has a larger distal portion to accommodate the basket, while the remainder of the sheath has a smaller, uniform diameter to improve fluid flow. These prior art designs proposed to improve fluid flow have several disadvantages. With a sheathless basket, the closed basket cannot be advanced from the ureteroscope, for example, to advance the basket in the closed state past an impacted stone and then open the basket beyond the stone. Additionally, control of basket opening and closing beyond the end of the ureteroscope is lost without a sheath. A ribbed sheath is of little practical advantage. Since standard polyimide sheaths used for stone baskets typically have wall thickness of only 0.003 inch or less, a ribbed design would have a negligible impact. A drive wire and control rod design has the disadvantage that it is inoperable outside of the endoscope making it very difficult to pretest the instrument prior to use. The tapered sheath does not have variable flexibility to match the articulating portion of a flexible ureteroscope to prevent loss of endoscope deflectability. Additionally, all of the embodiments disclosed in U.S. Patent Publ. No. 2004/0199048 use a 0.030 to 0.034 inch nitinol drive wire, which requires 2.3 to 2.6 Fr without a sheath.

An additional disadvantage of prior art tipless baskets is that multiple exchanges of retrieval and lithotripsy devices in the working channel of the ureteroscope lengthen the procedure and increase the chances of damage to the delicate instruments. The smallest of the commonly used laser fibers (272 μm, often referred to as 200 μm) has a sheath diameter of about 400 μm (1.2 Fr). It is only with this smallest size fiber and the smallest available tipless baskets (1.9 Fr) that both devices can simultaneously occupy the interior diameter of the working channel of a conventional ureteroscope. However, in this situation, the working channel is almost completely filled by the two devices, severely limiting irrigation flow. An unfortunate event that can occur is that a stone too large to remove intact cannot be released from the basket. When this happens and a laser fiber can be passed through the working channel, the stone can normally be fragmented so that the basket can be removed. However, if the sheath is too large to permit a laser fiber to be simultaneously passed through the working channel, the resolution of the situation can cause injury to the patient.

It would be desirable to provide a stone retrieval device for endoscopic retrieval procedures that provides improved fluid flow, permits sufficient flexible endoscope deflection, and is sized to share a single working channel with a laser fiber, without compromising device strength or functionality.

SUMMARY OF THE INVENTION

The present invention is a medical retrieval device and method used in endoscopic procedures to retrieve stones that has a shaft comprising a sheath with a lumen and a drive wire slidably disposed within the lumen for operating a stone entrapping mechanism on the distal end of the retrieval device. The shaft has an average outside diameter of less than 1.9 Fr. The shaft, sheath and drive wire each have proximal, intermediate and distal portions, and each of the corresponding portions are in generally similar locations along the longitudinal length of the device. The proximal portions of the shaft and the drive wire are preferably stiffer than the corresponding intermediate portions of the shaft and drive wire. The proximal and intermediate portions of the sheath have generally similar stiffnesses. The shaft reduces flow resistance within the working channel of an endoscope, increasing the flow of irrigation fluid in order to improve procedural visibility. The shaft varies in flexibility to match the requirements of a flexible endoscope and facilitate deflection of the endoscope.

In preferred embodiments, the shaft has an object entrapping mechanism extending from a distal end that comprises a basket that is substantially tipless. Preferably, at least a portion of the drive wire is formed from a shape memory material and has a plurality of cross sections at different longitudinal locations to create the differing stiffnesses along the longitudinal length of the drive wire.

The stone entrapping mechanism can be a substantially tipless basket, an extending tip basket, a grasping device, or other known configurations of a retrieval device.

Current flexible ureteroscopes typically have a single 3.6 Fr (1 Fr=0.33 mm), working channel inner diameter. Currently marketed tipless stone basket retrieval devices that can be used with these flexible ureteroscopes range from 1.9 Fr to 3.2 Fr. These sizes fill 53% to 89% of the diameter of a 3.6 Fr working channel, which significantly reduces irrigation flow.

A laser fiber having an outer diameter of 1.2 Fr cannot be simultaneously introduced into the 3.6 Fr diameter working channel with a retrieval device 2.4 Fr or greater. Consequently, only the smallest existing tipless basket retrieval devices are even able to be utilized simultaneously in a working channel of an ureteroscope with a laser fiber. As previously described, for existing retrieval devices having outer diameters between 1.9 and 2.3 Fr, the simultaneous introduction of the laser fiber and the retrieval device creates a situation in which the maneuverability and flexibility of the ureteroscope is compromised, and, more importantly, the ability to adequately disperse irrigation fluid through the working channel is significantly impacted because the diameters of the laser fiber and the retrieval device are greater than about 85% of the diameter of the working channel.

The present invention overcomes these problems by providing a flexible shaft with a sheath with an outer diameter that is sized smaller than 1.9 Fr and preferably similar in diameter to the small laser fibers commonly used in urology. As a result, the present invention reduces the constriction of irrigation flow within a single working channel that is caused by simultaneous use of both a stone retriever and irrigation.

In one embodiment, the present invention provides a medical retrieval device with a shaft that has a simpler construction and still increases deflection and irrigation. In one embodiment, the present invention provides a medical retrieval device with a shaft with a high flow sheath combined with a drive wire that varies in flexibility to match the capability of a flexible ureteroscope without substantially impairing the capacity of the scope to flex. In one embodiment, the present invention provides a medical retrieval device with a shaft that maximizes ease of insertion into Touhy Borst adapters, endoscopic valves or other similar ports used at the proximal end of the working channel. In one embodiment, the present invention provides a medical retrieval device with a shaft having a sheath and a drive wire combination that reduces kinking or buckling, increases longitudinal strength and/or provides a plurality of flexibilities needed for a flexible endoscope.

In one embodiment, the present invention provides a medical retrieval device having an optimized shaft to be used in conjunction with a tipless stone basket or grasper to retrieve stones located in a calyx of the kidney. In one embodiment, the present invention provides a medical retrieval device with a shaft having a sheath with a maximum outer diameter such that the medical retrieval device can be used simultaneously along side a laser fiber within in a single working channel and still allow for sufficient irrigation flow by together occupying less than about 80% of the average diameter within the working channel. In one embodiment, the present invention provides a medical retrieval device having a sheath that generally increases in outer diameter from proximal to distal portions along the longitudinal length of the device to reduce flow resistance within a proximal portion of said working channel, and also provide for greater strength associated with support and manipulation of the stone entrapping mechanism to facilitate receiving larger object entrapping mechanisms at the distal portion of the device.

The present invention provides a medical retrieval device having a sheath and basket combination that can improve small stone capture ability.

Further objects and advantages of preferred embodiments of the device described herein are that such preferred embodiments are safe, reliable, and easy to use. Still further objects and advantages will become apparent from a consideration of the ensuing description and drawings.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention.

FIG. 3a is a cross-sectional view of taken on line 3a-3a in FIG. 3.

FIG. 3b is an enlarged view of the distal end of FIG. 3 showing the intersecting area of the basket wires.

FIG. 3c is an end view of FIG. 3b.

FIG. 5a is a side view of the hub shown in FIGS. 3b and 3c.

FIG. 5b is end view of FIG. 5a.

FIG. 7 shows a view in perspective and partly in section of part of the shaft and the basket of FIG. 3.

FIGS. 7a, 7b, and 7c are cross-sectional views taken on lines 7a-7a, 7b-7b, and 7c-7c, respectively, in FIG. 7, but showing the cross-section of only the drive wire according to this invention.

FIG. 9 is a similar view as FIG. 7 but showing another embodiment of the drive wire.

FIGS. 9a, 9b, and 9c are cross-sectional views taken on lines 9a-9a, 9b-9b, and 9c-9c, respectively, in FIG. 9, but showing the cross-sections of only the drive wire.

FIGS. 10a, 10b, and 10c are cross-sectional views taken on lines 10a-10a, 10b-10b, and 10c-10c, respectively, in FIG. 10.

FIGS. 11a, 11b, and 11c are cross-sectional views taken on lines 11a-11a, 11b-11b, and 11c-11c, respectively, in FIG. 11.

FIGS. 12a, 12b, and 12c are cross-sectional views taken on lines 12a-12a, 12b-12b, and 12c-12c, respectively, in FIG. 12.

FIG. 13 is a similar view as FIG. 3b but showing another embodiment in which the wire is flattened at the very distal end of the basket.

FIGS. $13a_1$ and $13b_1$ are cross-sectional views taken on lines 13a-13a and 13b-13b, respectively, in FIG. 13.

FIGS. $13a_2$ and $13b_2$ are cross-sectional views of another embodiment taken on lines 13a-13a and 13b-13b, respectively, in FIG. 13.

FIG. 14 is an end view of FIG. 13.

Figures 15, 15A:
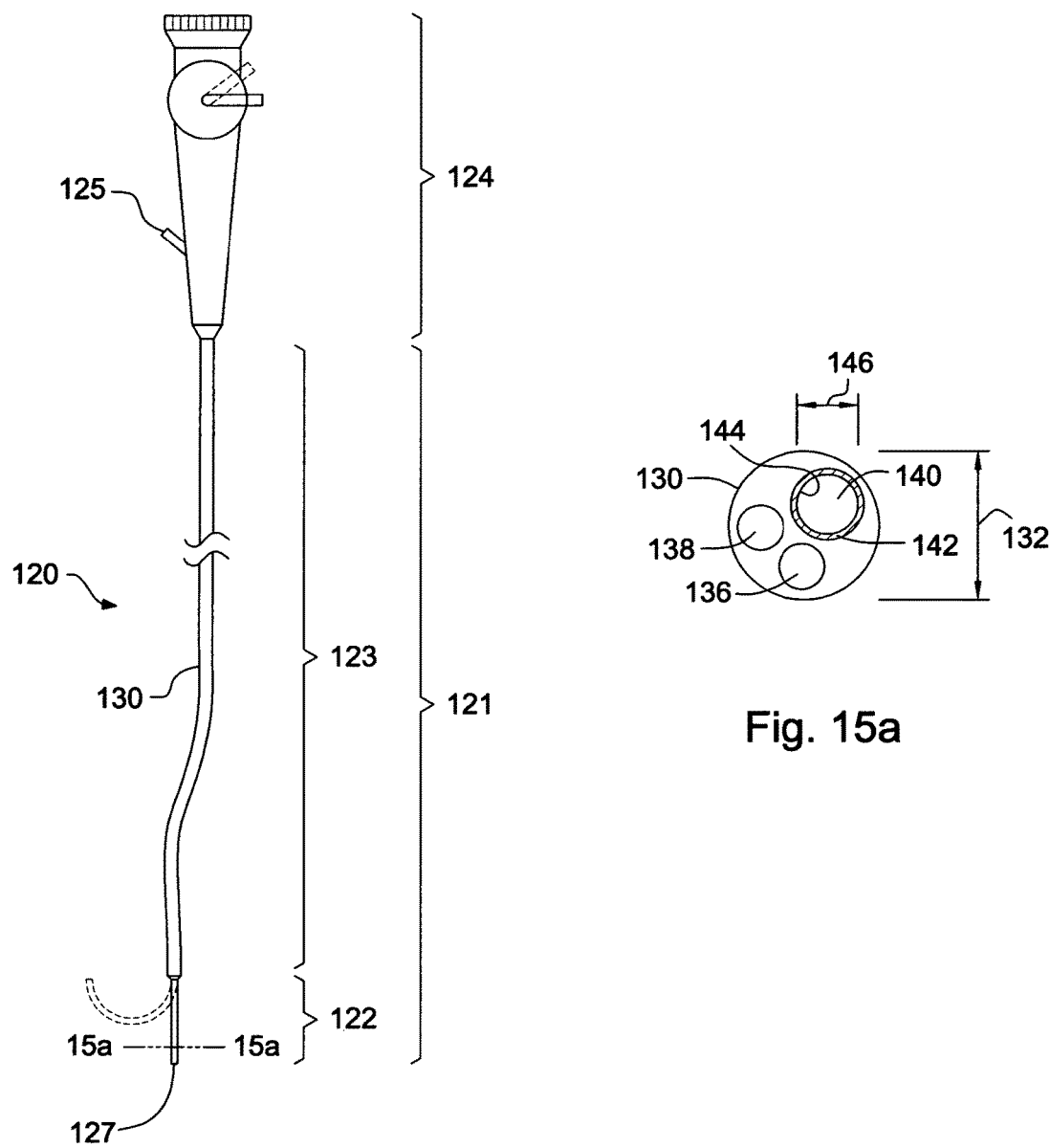

FIG. 15 is a side view of a typical flexible ureteroscope. The drawing is not to scale.

FIG. 15a is an enlarged cross-sectional view of FIG. 15 taken on line 15a-15a.

FIG. 16 is a table of flexible ureteroscope specifications.

Figure 17:
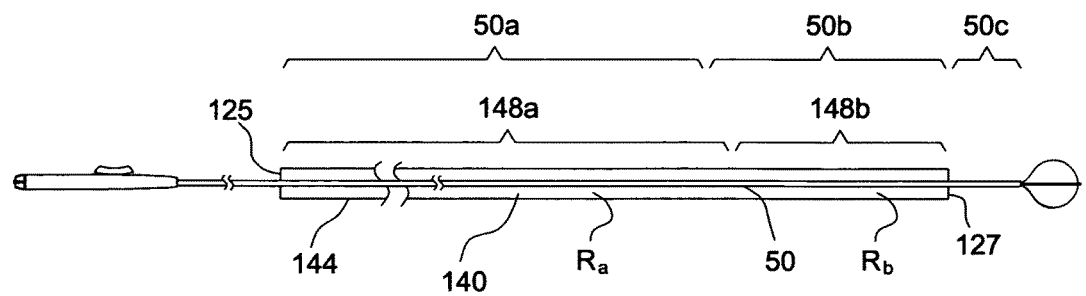

FIG. 17 is a longitudinal cross-sectional view of an endoscope working channel with a retrieval device according to the present invention positioned within the working channel.

Figure 17A:
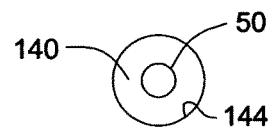

FIG. 17a is an end view of FIG. 17, but showing only the working channel and the outside diameter of the sheath of the retrieval device.

Figure 18:
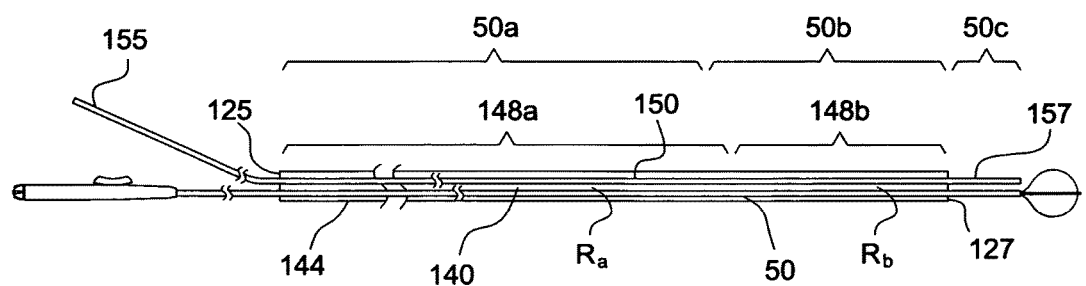

FIG. 18 is a longitudinal cross-sectional view of an endoscope working channel with a retrieval device according to the present invention and a laser fiber both positioned within the working channel.

Figure 18A:
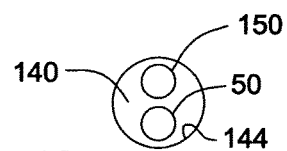

FIG. 18a is an end view of FIG. 18, but showing only the working channel and the outside diameters of the sheath of the retrieval device and the laser fiber.

Figure 19:
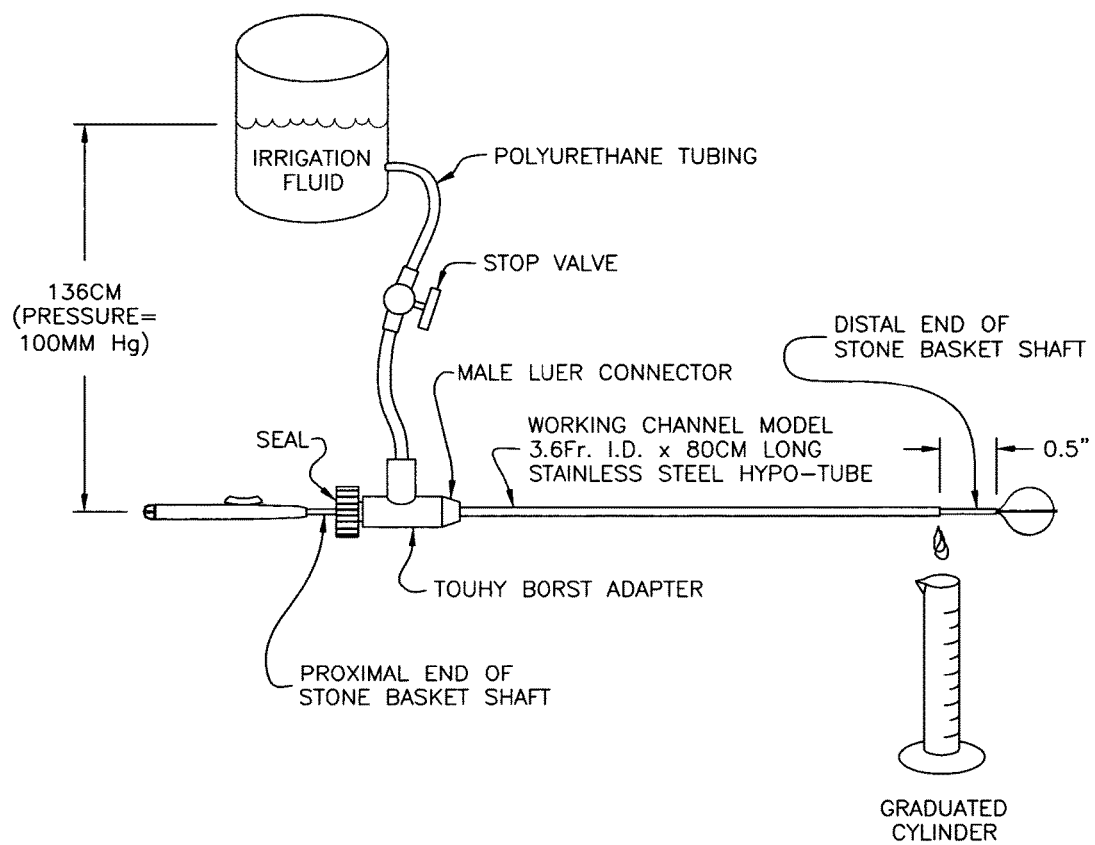

FIG. 19 is a side view of the bench test setup used to show an advantage of the present invention.

FIG. 20 is a table showing the results of irrigation flow testing.

DETAILED DESCRIPTION OF PREFERRED EMBODIMENTS

For purposes of describing the present invention, the following terms are specifically defined. A "grasping device" is defined as a filament or non-filament structure in which at least a portion of the structure separates at the distal end when open and comes together at the distal end during closure. Examples of such grasping devices are described in U.S. Patent Publ. Nos. 2002/0133170, 2003/0105488, 2003/0225419, and 2004/0215212, and U.S. Pat. Nos. 4,655,219, and 6,280,451, the disclosure of which are expressly incorporated by reference herein.

A "basket" is defined as a structure comprising multiple filaments that cross over, intersect, or are joined at the distal end when the basket is open. An "extending tip" basket has a distal end that extends significantly beyond the area where the filaments start to blend together. This could prevent a head-on approach to perpendicular tissue. Examples of extending tip baskets are shown in U.S. Patent Publ. No. 2003/0078593 and U.S. Pat. Nos. 4,927,426, 5,496,330, 6,168,603, and 6,190,394, the disclosure of which are expressly incorporated by reference herein.

A "substantially tipless" basket is generally defined as a basket in which the distance between the open space within the filaments and the distal end is minimized by the configuration of the wire and/or the joining means so that a head-on approach to perpendicular tissue is possible. This definition would include the basket described in U.S. Pat. No. 4,590,938 ("nipple bend") and also in U.S. Patent Publ. No. 2004/0133213 ("stub tip"), both of which are expressly incorporated by reference herein. The solid or rigid portion of the stub tip design has a longitudinal length that is generally 0.065 inch or less, preferably 0.050 inch or less and optimally 0.040 inch or less. A "substantially tipless" basket is more preferably defined to additionally include filaments that do not have distal blending to generally parallel positions when the basket is in an open position. Examples of these are shown in U.S. Pat. No. 5,057,114 ("suture joined"), U.S. Pat. No. 5,989,266 ("looped connection"), U.S. Pat. No. 6,159,220 ("knotted"), U.S. Pat. No. 6,626,915 ("unattached"), U.S. Pat. No. 6,224,612 ("unsecured protrusion"), and U.S. Pat. No. 6,527,781 ("cap/distal bend"), U.S. Patent Publ. No. 2003/0088254 ("wire collector"), and U.S. patent application Ser. No. 10/831,267 ("hub"), the disclosures of which are expressly incorporated by reference herein.

A "stone," also referred to as a calculus, is generally defined as an abnormal concretion in a human organ or duct, typically in the urinary or biliary systems. This would include, for example, kidney stones, ureteral stones, caliceal stones, gall stones and bile duct stones, and any fragments thereof.

FIGS. 1 to 4 show one embodiment of the invention. A medical retrieval device has a handle assembly 10, which has a longitudinal axis 11. Handle assembly 10 is comprised of an elongate handle base 20, a sliding portion or thumb slide 30, and a rotation means or spinner 40, all of which are preferably constructed of thermoplastic materials. Handle base 20 has a proximal end 21, distal end 22 and a length 23, which is between 5 and 20 cm. Handle base 20 is essentially hollow along longitudinal or long axis 11, with an internal bore and an opening 24 at distal end 22. A longitudinal slot 25 is located on a portion of the top surface of handle base 20, and has a proximal end 26 and a distal end 27. Thumb slide 30 is engaged with handle base 20 within slot 25 such that thumb slide 30 can be readily moved to any position within slot 25 between proximal end 26 and distal end 27, but cannot be inadvertently removed vertically or longitudinally from slot 25. The actuation of thumb slide 30 overlaps the area between proximal end 21 and distal end 22 of handle base 20. The total length of longitudinal travel of thumb slide 30 relative to handle base 20 is preferably 5 cm or less. Spinner 40 is rotatably engaged with handle base 20 at proximal end 21 by a snap fit, the use of a separate component such as a pin, or other suitable mechanisms, such that spinner 40 can rotate freely about longitudinal axis 11 relative to handle base 20, but cannot move longitudinally relative to handle base 20. A tube or sheath 50 has a proximal end 51, a distal end 52, and has a lumen through its entire length. Sheath 50 has a working length 53 that is generally between 80 and 200 cm, preferably 90 to 150 cm, and optimally 100 to 130 cm. Sheath 50 passes through opening 24, which is larger in diameter than sheath 50. Proximal end 51 of sheath 50 passes into a through hole in thumb slide 30 and is secured to thumb slide 30 using adhesive or another method of attachment. A stone entrapping mechanism or basket 60 is located adjacent to distal end 52 of sheath 50. A drive wire 70 has a proximal end 71 and a distal end 72. Drive wire 70 slidably extends through the lumen of sheath 50, with proximal end 71 of drive wire 70 extending past proximal end 51 of sheath 50. Proximal end 71 of drive wire 70 fits into a hole in spinner 40 and is secured using adhesive, friction fit, or another similar method of attachment. Basket 60 is attached to distal end 72 of drive wire 70. Sheath 50 is longitudinally movable relative to drive wire 70 and basket 60.

Referring to FIGS. 3a to 3c, the basket preferably consists of a plurality of flexible elements or wires 61a to 61d that are outwardly disposed about the longitudinal axis to form a space for entrapping objects when open. Basket 60 has an expandable diameter 80, which in its completely open state is generally between 6 and 24 mm, preferably 8 to 20 mm, and optimally 10 to 16 mm. Basket wires 61a to 61d may be constructed or formed of a shape memory material, such as nickel titanium alloy (for example, nitinol), stainless steel, or another material with similar properties, and preferably have a largest cross-sectional dimension that is typically between 0.003 and 0.015 inches. In preferred embodiments, there are four basket wires.

In the embodiment shown, basket wires 61a to 61d are constructed of round wire that has been slightly flattened to a thickness 81 and a width 82. In this embodiment, the ratio of width to thickness dimensions is approximately 1.1:1.0 to 1.5:1.0. Basket wires 61a and 61b are formed of a continuous strand or piece of wire, and basket wires 61c and 61d are formed of a second continuous strand or piece of wire. Both ends of each of the two continuous pieces of wire are attached to the distal end of the drive wire, with the remainder of the two wires forming two loops that are perpendicular to each other, and intersect at the distal end of basket 60. These two loops are connected at their distal intersecting area by means of a wire collector or hub 63, which is disposed at the distal end of basket 60. Hub 63 has four ports, passages, or holes 65a-65d passing through it radially that are spaced approximately 90° to each other. These radially disposed holes may be made by machining, laser cutting, punching, or any other method known in the art. Holes 65a-65d act as receiving structure for the basket wires, and may be sized to provide a friction fit, or binding interface, to secure the basket wires, or may be sized to allow the wires greater freedom of movement.

Figures 5A, 5B:
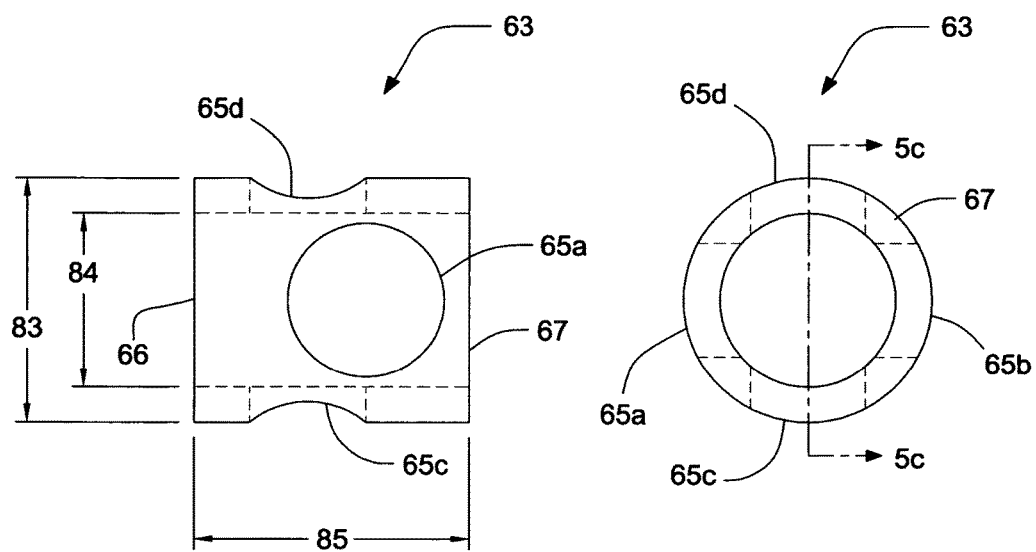
Figure 5C:
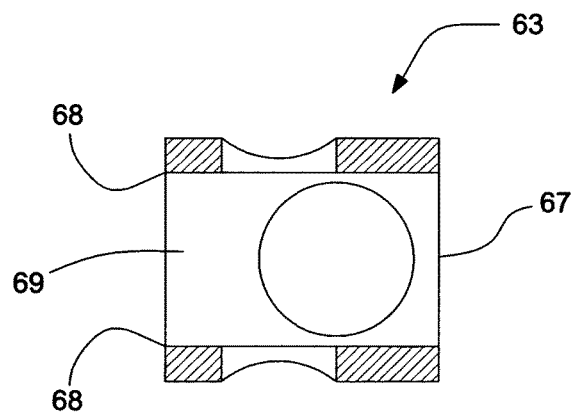
FIG. 5c is a cross-sectional view taken on line 5c-5c in FIG. 5b.
Figure 6:
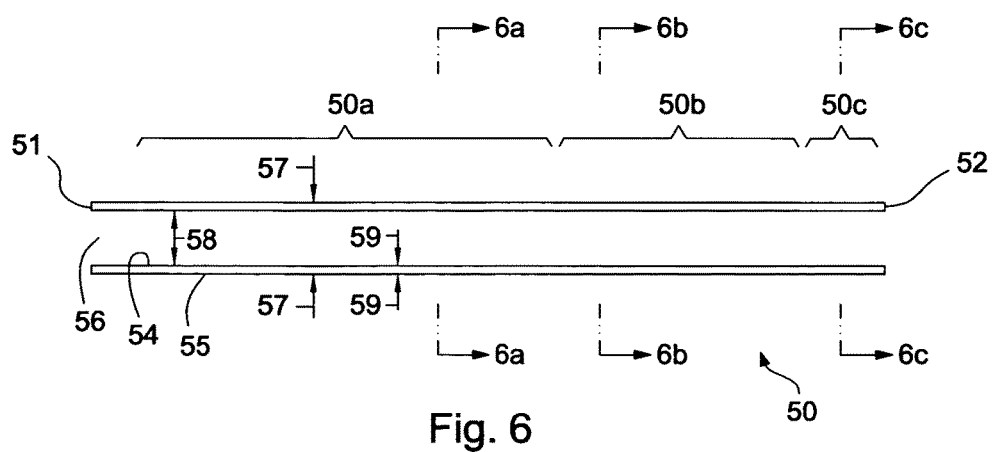
FIG. 6 is a longitudinal cross-sectional view of the sheath in accordance with the present invention.
Figure 6A:
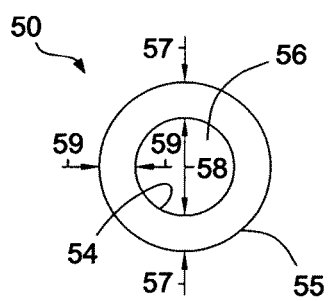
FIGS. 6a, 6b, and 6c are cross-sectional views taken on lines 6a-6a, 6b-6b, and 6c-6c, respectively, in FIG. 6.
Figure 6B:
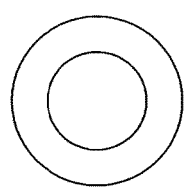
Figure 6C:
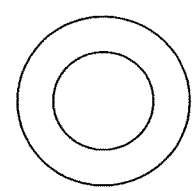

Referring to the embodiment shown in FIGS. 5a to 5c, hub 63 is in the shape of a hollow ring having an outside diameter 83, an inside diameter 84, and a cavity 69. Hub 63 is constructed of a rigid material such as stainless steel, nickel titanium alloy, or a material with similar properties; or of a flexible material, such as rubberized thermoplastic, silicone, or a material with similar properties. Hub 63 may be made from hypodermic tubing, or may be formed by machining, extruding, molding, casting or other processes known in the art. Hub 63 may be a substantially rigid body or a substantially flexible body. Hub 63 has a proximal end 66 and a distal end 67. At proximal end 66, inside diameter 84 and cavity 69 form an inwardly disposed contact element 68, which provides increased contact points for a generally spherical object to assist in retaining the object. Two holes 65a and 65b that are opposite each other are located closer to distal end 67 of hub 63, and the other two opposite holes 65c and 65d are located closer to proximal end 66 of hub 63. In preferred embodiments, hub 63 has a longitudinal length 85 of 0.040 inches or less, but preferably 0.020 inches or less.

Referring again to FIGS. 3b and 3c, the wire that forms basket wires 61a and 61b passes through the set of opposite holes 65a and 65b located closer to the distal end 67, and the wire that forms basket wires 61c and 61d passes through the set of opposite holes 65c and 65d located closer to the proximal end 66. Thus basket wires 61a to 61d extend from hub 63 in an orientation that is generally transverse to longitudinal axis 11 when basket 60 is in the open position. Hub 63 may or may not be secured to basket wires 61a to 61d using adhesive, solder, or another hardenable material, or by laser welding or any other method. Thus, the distal section of basket 60 in this embodiment has a substantially tipless configuration.

Referring again to FIGS. 1 to 3, the basket wires are formed about longitudinal axis 11 by means known in the art to the desired basket shape and size. Opposing basket wires 61a and 61b are substantially planar and opposing basket wires 61c and 61d are substantially planar. Basket 60 has a generally bulbous form at its distal end, which is defined by hub 63. The distal portion of the basket is substantially hemispherical in shape.

Referring now to FIGS. 6, 6a, 6b, and 6c, sheath 50 has a proximal portion 50a, an intermediate portion 50b, and a distal portion 50c. Proximal portion 50a has a length that is generally between 60 and 190 cm, preferably 70 to 140 cm, and optimally 85 to 120 cm. Intermediate portion 50b has a length that is generally greater than 6 cm, preferably 8 to 16 cm, and optimally 10 to 14 cm. Distal portion 50c has a length that is generally between 0 and 10 cm, preferably 0 to 4 cm, and optimally 0 to 2 cm. Sheath 50 has an inside surface 54, an outside surface 55, a lumen 56, an outside diameter 57, and a wall thickness 59. Lumen 56 has an inside diameter 58, which is generally between 0.011 and 0.020 inches, preferably 0.013 to 0.019 inches, and optimally 0.015 to 0.018 inches. In this embodiment, outside diameter 57 is generally constant and uniform throughout proximal portion 50a, intermediate portion 50b, and distal portion 50c, but could vary within or between portions. Outside diameter 57 or its average is generally less than 1.9 Fr, preferably less than 1.8 Fr or less, and optimally less than 1.7 Fr. Outside diameter 57 or its average is generally greater than 0.4 Fr, preferably greater than 0.8 Fr, and optimally greater than 1.1 Fr. Inside diameter 58 and wall thickness 59 are generally constant and uniform throughout proximal portion 50a, intermediate portion 50b, and distal portion 50c. Wall thickness 59 is generally between 0.0005 and 0.006 inches, preferably 0.001 to 0.003 inches, and optimally 0.0015 to 0.0025 inches. Sheath 50 is preferably constructed of polyimide, nickel titanium, polyetheretherketone (PEEK), or another suitable flexible material or combination of materials. In this embodiment, sheath 50 has generally uniform flexibility throughout proximal portion 50a, intermediate portion 50b, and distal portion 50c. Sheath 50 has sufficient strength and rigidity to resist deformation as the basket is moved relative to the sheath. Inside surface 54 and outside surface 55 may or may not be coated with material having a low friction coefficient, such as polytetrafluoroethylene (PTFE), fluorinated ethylenepropylene (FEP) or other suitable materials or substances known in the art. These low-friction materials are included in the composition of the sheath wall during manufacturing or applied to the surface of the sheath after the sheath is manufactured. Other materials may be included in one or more layers of the sheath, such as a braid or coil of nickel titanium or stainless steel.

Referring to FIGS. 7, 7a, 7b, and 7c, drive wire 70 is joined to the basket wires within a connecting tube 73, which is constructed of hypodermic tubing made of stainless steel, nickel titanium alloy, or another material. The tube is preferably secured to the wires by swaging, which not only secures the wires within connecting tube 73, but also reduces the diameter of the tube. Alternatively, other joining methods known in the art may be used, such as soldering, crimping, welding, interference fit, adhesive bonding, or other known joining methods. The diameter of connecting tube 73 is preferably 0.019 inch or less. The distal end of connecting tube 73 defines distal end 72 of the drive wire. Drive wire 70 has a smaller diameter segment 74 that is located proximal to connecting tube 73. Smaller diameter segment 74 has a diameter of approximately 0.004 to 0.012 inches, which is smaller than the balance of drive wire 70. The length of smaller diameter segment 74 is generally greater than 4 cm, preferably greater than 6 cm, and optimally greater than 8 cm. Between smaller diameter segment 74 and the larger diameter portion of drive wire 70 is a tapered segment 75, which has a length of approximately 0.25 to 3 inches, but could also be much longer than 3 inches. The remainder of drive wire 70 located proximal to tapered segment 75 has a generally uniform diameter that is generally between 0.006 and 0.018 inches, preferably 0.008 to 0.016 inches, and optimally 0.010 to 0.014 inches, to provide sufficient strength for opening and closing the basket.

Drive wire 70 may be constructed or formed of a shape memory material, such as nickel titanium alloy, stainless steel, or another material with similar properties. Smaller diameter segment 74 and tapered segment 75 may be made by centerless grinding, swaging, or any other similar method. Drive wire 70 may be coated with PTFE, FEP, or another low-friction material, or other lubricious substance known in the art. Smaller diameter segment 74, along with the smaller end of tapered segment 75, provides greater flexibility in this portion of the drive wire than the remaining larger diameter portions, which are more rigid. This more flexible or intermediate portion of the drive wire is generally located within intermediate portion 50b of sheath 50. Connecting tube 73 comprises a distal portion of the drive wire. This distal portion has a length that is generally 0 to 3 cm, preferably 0 to 2 cm and optimally 0 to 1 cm. The larger end of tapered segment 75 along with the balance of drive wire 70 located proximal to it, comprise a proximal portion of the drive wire. This configuration results in the shaft, consisting of drive wire 70 within sheath 50, having an intermediate portion near the distal end that is more flexible than the remainder of the shaft. The flexible intermediate portion of the shaft is capable of bending back upon itself or is capable of bending around a small diameter, such as 6 to 20 mm, preferably 17 mm. The intermediate portion of the shaft is sufficiently flexible so that when located within the articulating portion of a flexible ureteroscope or endoscope, the deflection capability of the scope is not significantly restricted. The proximal portion of the drive wire is generally longitudinally aligned within the proximal portion of the sheath, and the distal portion of the drive wire is generally longitudinally aligned within the distal portion of the sheath, in at least a part of the travel of the drive wire within the sheath.

An additional advantage of smaller diameter segment 74 is that the diameter of connecting tube 73 can be reduced, possibly to a diameter similar to or less than the diameter of the larger proximal portion of drive wire 70. This has the desirable result of permitting both the sheath inside diameter and outside diameter to be reduced. For at least 20 cm in length, the outside diameter of the drive wire is generally greater than 70% of the sheath lumen inside diameter, preferably greater than 80%, and optimally greater than 85%. By reducing the gap between the drive wire and the sheath, the sheath is made more resistant to buckling or kinking, despite its small diameter and thin wall. The smaller distal diameter of the shaft also allows insertion into Touhy Borst adapters, endoscopic valves or other similar ports used at the proximal end of the working channel, without the need for a separate introducer. The solid, single piece drive wire of this embodiment transmits torque efficiently, allowing precise rotational control of the basket.

Figure 1:
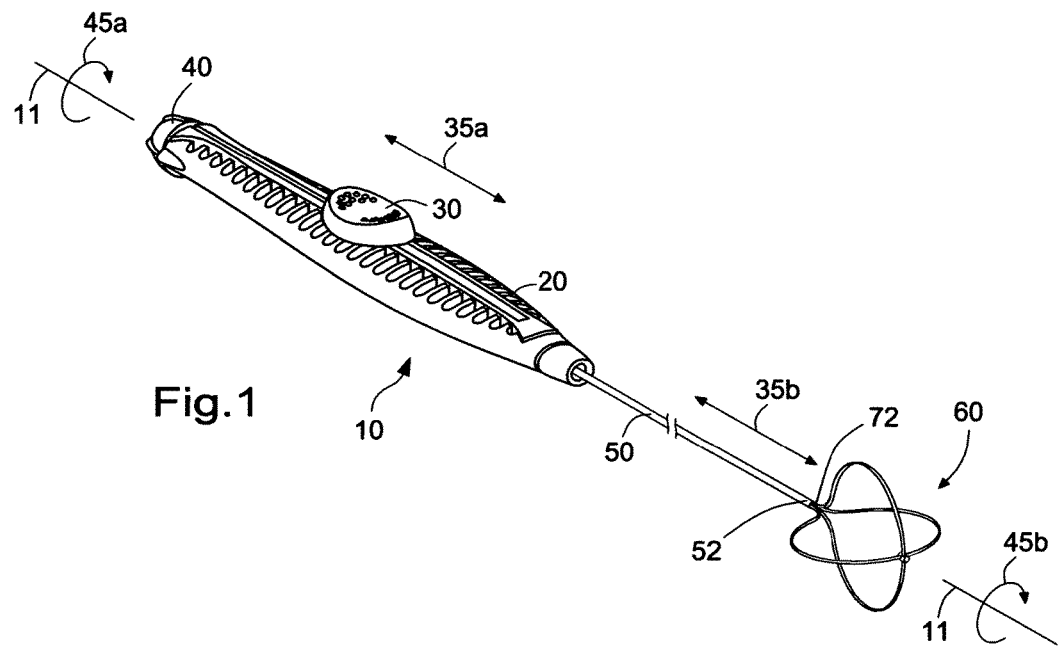
FIG. 1 is an isometric view of an embodiment of the present invention.
Figure 2:
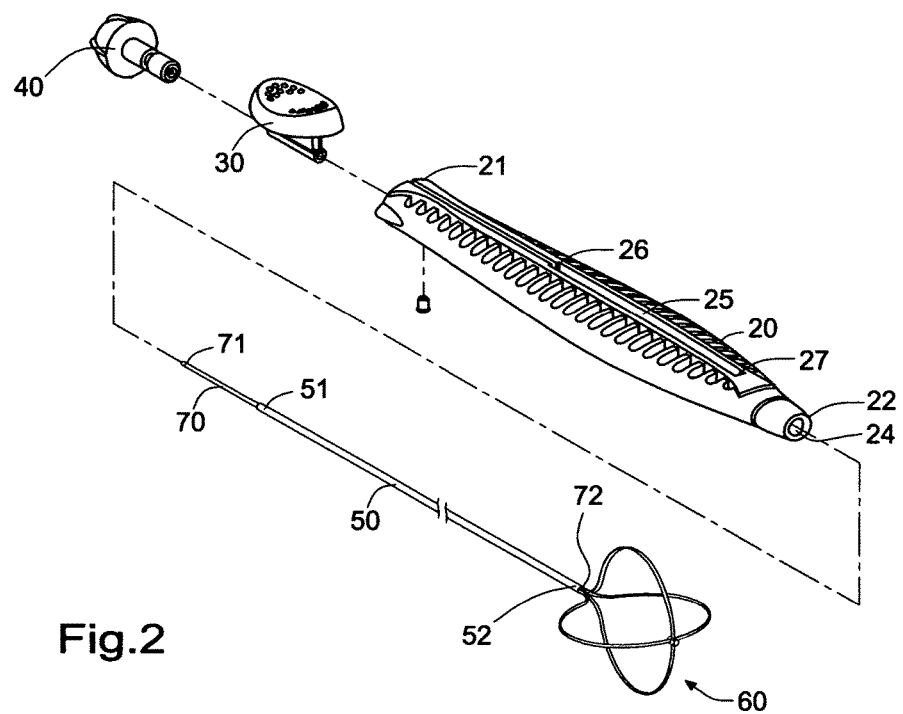
FIG. 2 is an exploded isometric view of FIG. 1.
Figure 3:
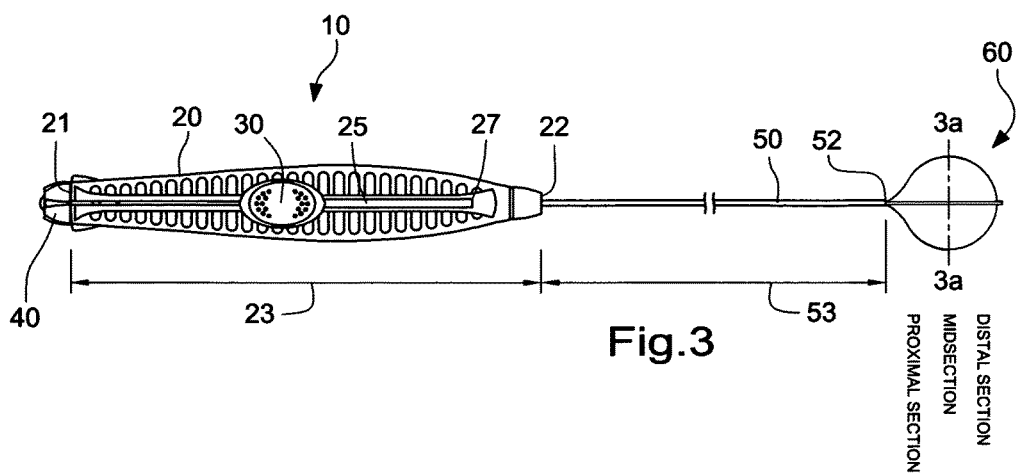
FIG. 3 is a top view of FIG. 1 showing the basket in the extended or open position, and also shows the proximal, mid, and distal sections of the basket.
Figure 4:
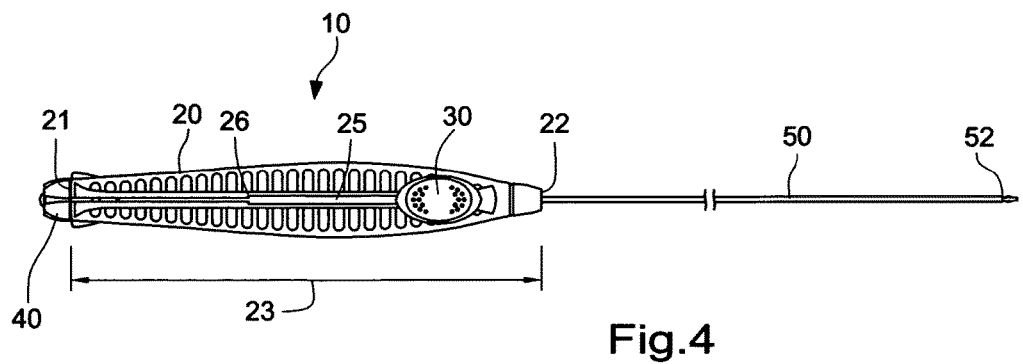
FIG. 4 is a top view of FIG. 1 showing the basket in the retracted or closed position.

To operate the device, the user wraps four fingers of one hand partially around handle base 20, but not overlapping thumb slide 30. The tip of the thumb of the same hand is placed on thumb slide 30. Referring to FIGS. 1 and 3, basket 60 is in the open or expanded position. In this position, thumb slide 30 is located at proximal end 26 of slot 25. To actuate the device to the closed or retracted position, the user extends the thumb outward from the hand while maintaining contact between the thumb and thumb slide 30 and keeping handle base 20 stationary in the hand. This action causes thumb slide 30 to slide within slot 25 toward distal end 27 (arrow 35*a*). This longitudinal movement of thumb slide 30 relative to handle base 20 propels sheath 50 over drive wire 70 (arrow 35*b*). This enables longitudinal movement of sheath 50 relative to basket 60, forcing basket 60 to collapse and become enclosed within sheath 50. When thumb slide 30 rests at distal end 27 of slot 25, basket 60 is in the closed or retracted position within sheath 50, as shown in FIG. 4. The distal end of basket 60, including hub 63, may retract completely within sheath 50, or may be sized such that it will not fit within the lumen of sheath 50, but stops adjacent to distal end 52 of sheath 50. In the latter case, the tip configuration and sizing must be such that the device in its fully closed position will pass through the working channel of the endoscope used. If, for example, the object the device is being used to retrieve is a kidney stone located within a calyx of the kidney, the device is introduced in this retracted position through the working channel of an endoscope into the kidney until the retracted basket emerges from the tip of the endoscope in the proximity of the kidney stone. The user then pulls the thumb back toward the hand, sliding thumb slide 30 back toward proximal end 26 of slot 25 (arrow 35*a*). This action pulls sheath 50 back relative to drive wire 70 and basket 60 (arrow 35*b*). Basket 60 is then exposed and resumes its expanded shape, as shown in FIGS. 1 and 3. At minimum, the actuation mechanism comprises the sheath and drive wire, which are longitudinally movable relative to each other in order to effect opening and closing of the basket.

Handle assembly 10 is then manipulated in order to entrap the stone within basket 60. Longitudinal manipulation of basket 60 relative to the object is accomplished by pushing or pulling handle assembly 10 along longitudinal axis 11. Rotational positioning of basket 60 is accomplished by grasping spinner 40 with the thumb and forefinger of the user's second hand, and rotating spinner 40 about longitudinal axis 11 (arrow 45*a*), relative to handle base 20, which is kept stationary with the first hand. This causes drive wire 70 to rotate within sheath 50, and basket 60 to rotate relative to sheath 50 the same amount in the same direction (arrow 45*b*). Once the stone has been engaged within basket 60, the user then pushes thumb slide 30 forward part way toward distal end 27 of slot 25 until basket 60 is partially closed in order to securely hold the stone. The device and the endoscope are then simultaneously withdrawn from the patient, holding thumb slide 30 stationary relative to handle base 20 to keep the stone secured within basket 60.

Figure 8A:
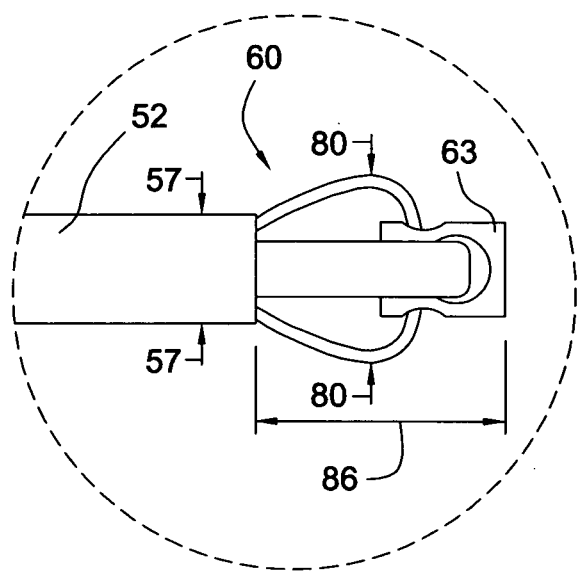
FIG. 8a is an enlarged view of the distal end of FIG. 4 showing the basket in the retracted or closed position.
Figure 8B:
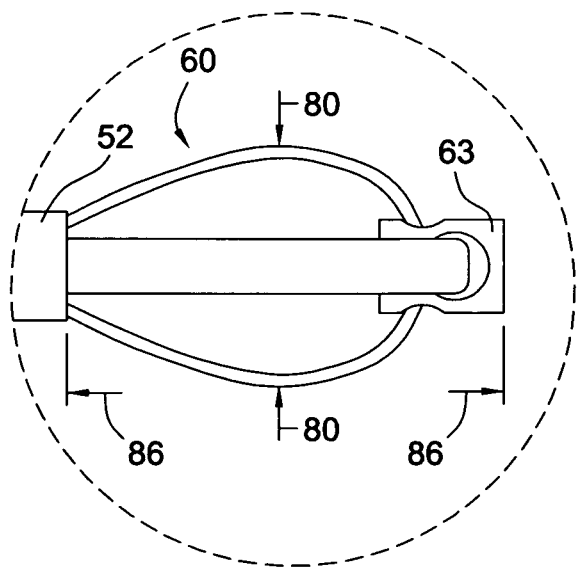
FIG. 8b is an enlarged view of the distal end of FIG. 4 showing the basket in a partially retracted or closed position.

FIG. 8*a* shows distal end 52 of sheath 50 and basket 60 in the fully closed or retracted position. Basket 60 has an extendable length 86 that is defined as the distance from distal end 52 of sheath 50 to the distal end of hub 63. In this embodiment, the basket does not retract completely into the sheath, and when the thumb slide reaches the travel limit or the distal section of the basket is prevented by size from further entering the sheath lumen, extendable length 86 is preferably 0.025 to 0.25 inches, and basket diameter 80 is less than 3.6 Fr, but greater than the sheath diameter at the distal end or distal portion. FIG. 8*b* shows a similar view as FIG. 8*a*, but with the basket in a partially closed state, where extendable length 86 and basket diameter 80 are both greater than when the basket is fully closed. In this embodiment, when extendable length 86 is extended at most 3 mm, basket diameter 80 generally exceeds 1.4 times sheath diameter 57 of the distal portion of sheath 50, preferably exceeds 1.6 times, and optimally exceeds 2.0 times sheath diameter 57 of the distal portion of sheath 50. This configuration has a number of advantages. First, the sheath diameter can be minimized to improve fluid flow. Second, the naturally open configuration of the distal end of the basket even when just slightly extended from the end of the sheath provides improved ability to capture and retain very small objects, such as small stones and stone fragments, than prior art tipless baskets that tend to pinch closed at the distal end when retracted.

It can be seen that the retrieval device according to one embodiment of the present invention provides a sheath that is sized smaller than prior art sheaths. Several factors make this reduced diameter possible. The drive wire has reduced diameter at the distal end, which makes possible a reduced diameter for the connecting tube used to join the drive wire to the baskets wires. The connecting tube is attached preferably by swaging, which further reduces the diameter of the tube. These improvements reduce the overall diameter of the drive wire, thereby making possible the reduction of the sheath inside diameter. The uniform flexibility of the sheath allows its wall thickness to be minimized. The reduced diameter sheath reduces the constriction of irrigation flow within a single endoscope working channel that is used simultaneously for both the retrieval device and irrigation. The resulting improved irrigation fluid flow allows for greater visibility in the field of view, facilitating rapid stone retrieval and potentially improving stone retrieval success rates.

It can also be seen that the retrieval device according to one embodiment of the present invention provides a shaft that varies in flexibility to match the capability of a flexible ureteroscope or endoscope. The flexible portion of the shaft coincides and deflects with a bending or deflectable portion of a flexible endoscope without substantially impairing the capacity of the scope to flex. The flexible portion of the shaft is sufficiently flexible so as permit generally unimpeded flexure of the deflectable portion of a flexible endoscope. This is made possible by the reduced diameter of the portion of the drive wire that is normally located within the deflecting portion of a flexible scope.

It can also be seen that one embodiment of the present invention provides a substantially tipless basket that can retrieve stone-like objects that are positioned in difficult to reach locations, such as kidney stones located in a calyx of the kidney. This configuration also serves to reduce trauma to body tissue, such as the kidney.

It can also be seen that one embodiment of the present invention provides a sheath for a retrieval device that increases irrigation flow and maximizes deflection but is of simpler construction than prior art sheaths such as in U.S. Pat. Nos. 6,325,807 and 6,398,791, and U.S. Patent Publ. No. 2004/0199048, which are incorporated herein by reference.

It can further be seen that one embodiment of present invention provides a sheath and drive wire combination that reduces kinking or buckling of the sheath and allows insertion into Touhy Borst adapters, endoscopic valves or other similar ports used at the proximal end of the working channel, without the need for a separate introducer.

It will be appreciated that one embodiment of the present invention is particularly well suited for a tipless stone basket used to retrieve stones located in a calyx of the kidney.

Another embodiment of the drive wire is shown in FIGS. 9, 9a, 9b, and 9c. Drive wire 70 comprises a solid wire section that has a smaller diameter segment 74 and a tapered segment 75, a connecting tube 73, a twisted strand or stranded section 76, and a collar 77. Smaller diameter segment 74 has a length of approximately 2 inches or less and a diameter of approximately 0.004 to 0.012 inches. Between smaller diameter segment 74 and the larger diameter proximal portion of drive wire 70 is tapered segment 75, which has a length of approximately 3 inches or less. The portion of drive wire 70 located proximal to tapered segment 75 has a generally uniform diameter that is generally between 0.006 and 0.018 inches, preferably 0.008 to 0.016 inches, and optimally 0.010 to 0.014 inches, to provide sufficient strength for opening and closing the basket. The solid wire section of drive wire 70 may be constructed or formed of a shape memory material, such as nickel titanium alloy, stainless steel, or another material with similar properties. Smaller diameter segment 74 and tapered segment 75 may be made by centerless grinding, swaging, or any other similar method. The basket wires extend past the proximal end of the basket, through collar 77, and are joined to smaller diameter segment 74 within connecting tube 73 by swaging or other joining methods known in the art, such as soldering, crimping, welding, interference fit, adhesive bonding, or other known joining methods. Connecting tube 73 and collar 77 are constructed of hypodermic tubing made of stainless steel, nickel titanium alloy, or another material. Collar 77 is attached to and secures the basket wires together to define the proximal end of basket 60. The distal end of collar 77 defines distal end 72 of the drive wire. Collar 77 is attached to the basket wires preferably by swaging, which not only secures the wires within collar 77, but also reduces the diameter of the collar. Alternatively, other joining methods known in the art may be used, such as soldering, crimping, welding, interference fit, adhesive bonding, or other known joining methods. The wires between collar 77 and connecting tube 73 are twisted together to form stranded section 76. When the basket wires are made of a nickel titanium alloy, such as nitinol, sufficient heat is applied to stranded section 76 after twisting to retain the stranded configuration, without compromising the resilient properties of the wire. The length of stranded section 76 is generally greater than 4 cm, preferably greater than 6 cm, and optimally greater than 8 cm. In this embodiment, the basket wires have a round cross section with diameter of generally 0.001 to 0.007 inches, preferably 0.002 to 0.006 inches, and optimally 0.003 to 0.005 inches. Part or all of drive wire 70 including stranded section 76 may or may not be coated with PTFE, FEP, or another low-friction material, or other lubricious substance known in the art. Stranded section 76 provides greater flexibility than other parts of drive wire 70 located proximal to connecting tube 73. This more flexible stranded section 76 is located within intermediate portion 50b of sheath 50. This configuration results in the shaft, consisting of drive wire 70 including stranded section 76 within sheath 50, having an intermediate portion, near the distal end, that is more flexible than the remainder of the shaft. The combination of the longer solid wire section and the shorter stranded section transmits torque efficiently, allowing precise rotational control of the basket. Several variations of this embodiment are possible. For example, the stranded section could consist of some, but not all, of the basket wires. Basket wires not included in the stranded section would terminate at the collar rather than the connecting tube. In another embodiment, the basket wires are similarly used to form a more flexible portion, but are not twisted together, resulting in a multi-strand configuration. In some embodiments, the collar could be omitted. Alternatively, the stranded section and basket wires could be constructed from separate pieces of wire, which may differ in number, size, and cross section. In this case, the collar would be used to join the basket wires to the stranded section. Additionally, the basket wires could have other cross sections or varying cross sections, or could each be constructed of a strand consisting of two or more wires.

Several other embodiments of a drive wire with a flexible portion are contemplated. For example, the drive wire could be ground in a stepped fashion rather than tapered. In another embodiment, greater flexibility in a portion of the drive wire could be made by removing some of the material by other methods, such as by forming grooves or notches in the wire. Such grooves or notches could be in the form of a helical shape around the long axis of the drive wire. The amount of flexibility could be varied by varying the depth and/or spacing of the grooves or notches. In another embodiment, the flexible portion is constructed of a helical coil formed of wire made of nickel titanium alloy, stainless steel, or another material with similar properties. The coil is joined at its proximal end to the drive wire and at its distal end to the basket wires with or without the use of connecting tubes or collars, by swaging, soldering, crimping, welding, interference fit, adhesive bonding, or other known joining methods. In yet another embodiment, the drive wire is constructed from two or more pieces of wire that are twisted together. One or more of the wires do not span the entire length of the drive wire, but terminate at a location approximately 2 to 6 inches from the distal end of the drive wire. Thus, the twisted strand drive wire has two portions consisting of different numbers of wires. The distal portion, having fewer wires, is more flexible than the remainder of the drive wire. In still another embodiment, the entire drive wire is constructed of some or all of the continuous pieces of wire that form the basket wires (multi-strand), which may or may not be twisted together in the drive wire section. In this embodiment, a connecting tube is not needed, but a collar or other securing means may be used to define the proximal end of the basket. The entire drive wire of this embodiment is more flexible than a similarly sized solid wire of the same material. In all of these embodiments, the more flexible portion of the drive wire, other parts of the drive wire, or all of the drive wire may be enclosed within a coil or another flexible covering.

Figure 10:
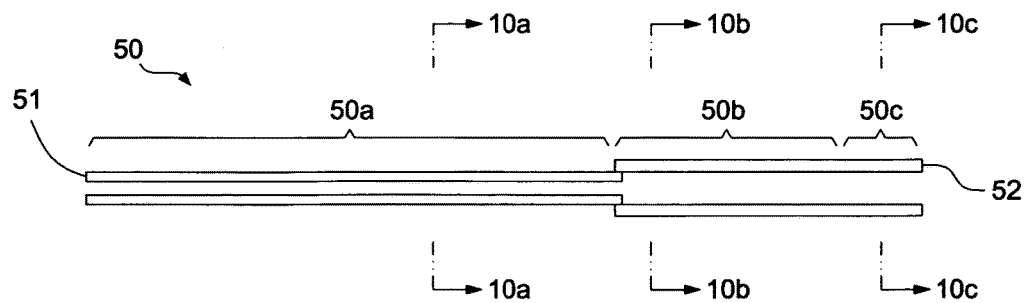
FIG. 10 is a longitudinal cross-sectional view of another embodiment of the sheath.
Figure 11:
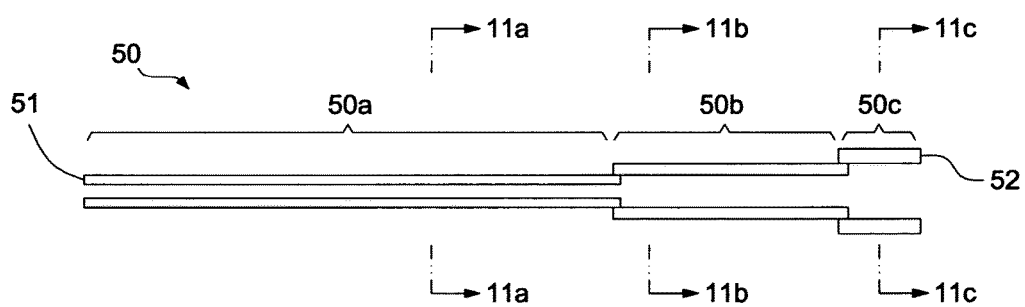
FIG. 11 is a longitudinal cross-sectional view of yet another embodiment of the sheath.
Figure 12:
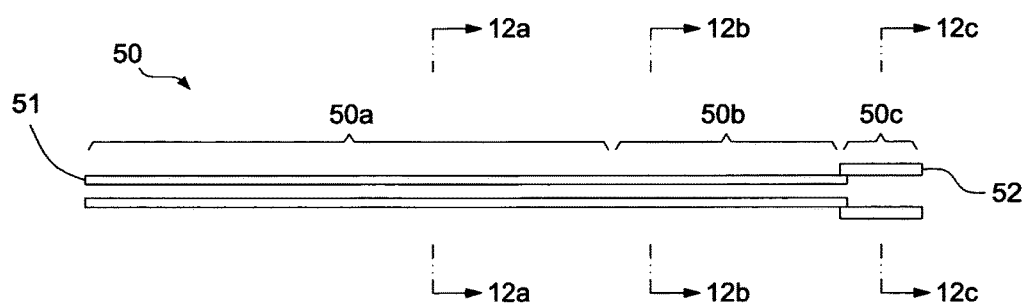
FIG. 12 is a longitudinal cross-sectional view of still another embodiment of the sheath.

Other embodiments of the sheath are shown in FIGS. 10, 11, and 12, with their respective cross sections shown in FIGS. 10a-10c, 11a-11c, and 12a-12c. Sheath 50 has a proximal portion 50a, an intermediate portion 50b, and a distal portion 50c, all having lengths as detailed in the description for FIG. 6. Each portion has an inside diameter, an outside diameter and a wall thickness. The wall thickness is as detailed in the description for FIGS. 6, 6a, 6b, and 6c.

One embodiment shown in FIGS. 10, 11, and 12 is that the average outside diameter of distal portion 50c is greater than the average outside diameter of proximal portion 50a. The average outside diameter of proximal portion 50a is generally less than 1.9 Fr, preferably less than 1.8 Fr, and optimally less than 1.7 Fr. In another embodiment, the outside diameter of distal portion 50c is generally greater than 1.9 Fr, preferably greater than 1.8 Fr, and optimally greater than 1.7 Fr. In another embodiment, the difference between the outer diameters is generally greater than 0.3 Fr, preferably greater than 0.5 Fr, and optimally greater than 0.7 Fr.

Another embodiment shown in FIGS. 10, 11, and 12 is that the inside diameter of distal portion 50c is greater than the inside diameter of proximal portion 50a. The inside diameter of proximal portion 50a is generally less than 0.021 inches, preferably less than 0.019 inches, and optimally less than 0.017 inches. The inside diameter of distal portion 50c is generally greater than 0.021 inches, preferably greater than 0.019 inches, and optimally greater than 0.017 inches. In another embodiment, the difference between the inside diameters is generally greater than 0.003 inches, preferably greater than 0.006 inches, and optimally greater than 0.009 inches.

There are several other embodiments shown in FIGS. 10, 11, and 12. The outside diameter and/or inside diameter may be the same in intermediate portion 50b and distal portion 50c, as shown in FIG. 10. The outside diameter and/or inside diameter of intermediate portion 50b may be different than both proximal portion 50a and distal portion 50c, as shown in FIG. 11. The outside diameter and/or inside diameter may be the same in intermediate portion 50b and proximal portion 50a, as shown in FIG. 12.

In the embodiments shown in FIGS. 10, 11, and 12, the different diameter portions of the sheath are separate components that are joined by adhesive bonding or another suitable method. The smallest diameter portions are preferably constructed of polyimide, or another suitable flexible material or combination of materials. The larger diameter portions may be constructed of polyimide, a coil made from stainless steel or nickel titanium alloy wire, or another suitable flexible material or combination of materials. The inside surface and the outside surface of some or all portions of the sheath may or may not be coated with material having a low friction coefficient, such as PTFE, FEP or other suitable materials known in the art. These low-friction materials are included in the composition of the sheath wall during manufacturing or applied to the surface of the sheath after the sheath is manufactured. In these embodiments, the larger inside diameters at the distal end of the sheath are sized to receive the basket in its closed state, along with the components needed to attach the basket to the drive wire and define the proximal end of the basket, such as a connecting tube and collar. When part or all of the drive wire is of smaller diameter than some or all of these components, the proximal portion of the sheath, and possibly the intermediate portion of the sheath, can have a smaller inside diameter, and thus a smaller outside diameter. By thus sizing each portion of the sheath to accommodate the components located within that portion of the sheath, the outside diameter of at least the proximal portion, which accounts for most of the length of the sheath, can be reduced, thereby improving irrigation fluid flow. In other embodiments, sheaths with portions having different diameters, such as those shown in FIGS. 10, 11, and 12, consist not of separate components that are joined together, but of a single continuous piece having portions with different diameters. The sheath may be manufactured with portions of different diameters, or modified after manufacture to expand or reduce the diameters of certain portions.

Referring to FIGS. 13 and 14, another embodiment of the basket is shown, in which a section of the basket wires at the distal end of the basket is flattened or has a reduced radial dimension. For example, if the basket wires are constructed of round wires, as shown in FIG. 13$a_1$, width 82 is equal to thickness 81. The wire diameter is generally between 0.001 and 0.007 inches, preferably 0.002 to 0.006 inches, and optimally 0.003 to 0.005 inches. A section of the basket wires within and immediately surrounding hub 63 are flattened so that width 82 is greater than thickness 81, as shown in FIG. 13$b_1$, with typical width to thickness ratios of 1.1:1 to 5:1. In this embodiment the flattened section thickness 81 is generally 0.0005 to 0.005 inches, preferably 0.001 to 0.004 inches, and optimally 0.0015 to 0.003 inches, and width 82 is generally 0.002 to 0.016 inches, preferably 0.003 to 0.014 inches, and optimally 0.004 to 0.012 inches. This reduces the amount of strain in the basket wire in an area that receives the most deformation as the basket is retracted into the sheath, and also allows the basket diameter in the fully closed position to be reduced.

In another embodiment, shown in FIG. 13$a_2$, the basket wires are made of round wire that has been slightly flattened so that width 82 is slightly greater than thickness 81. In this embodiment, the basket wire thickness 81 is generally 0.001 to 0.007 inches, preferably 0.002 to 0.006 inches, and optimally 0.003 to 0.005 inches, and width 82 is generally 0.002 to 0.014 inches, preferably 0.004 to 0.012 inches, and optimally 0.006 to 0.010 inches. A section of the basket wires within and immediately surrounding hub 63 are flattened, as shown in FIG. 13$b_2$, so that the width in this section is greater than the width in the balance of the basket wire, and the thickness in this section is less than the thickness in the balance of the basket wire. The width and thickness of the flattened section for this embodiment have similar dimensions to the flattened area described for FIG. 13$b_1$. In other embodiments, the entire length of the basket wires may be rolled, shape drawn, or flattened, with typical width to thickness ratios of 1.1:1 to 5:1. In another embodiment, the basket wires may be round over their entire length. In yet another embodiment, the basket wires may each consist of two or more wires twisted together to form a strand.

While certain specific embodiments of basket 60 have been discussed, several other embodiments would function equally well with the sheath and drive wire according to the present invention. Any of the prior art tipless baskets, other designs of tipless baskets and many types of baskets that are not substantially tipless, as well as other configurations, such as grasping devices, could also be used with the sheath and drive wire of the present invention and gain the benefits described herein.

Many other embodiments of the handle are also possible, such as other thumb slide designs, three ring style handles, and other handles known in the art. The sheath may alternatively be attached to the handle base and the drive wire to the thumb slide or other actuation mechanism. In this configuration, the drive wire is pulled back relative to the sheath to close the basket, rather than the sheath extended over the drive wire and basket. The spinner may be omitted. One or both of the sheath and the drive wire may be removably attached to the handle. The length of travel of the thumb slide could be defined other than by the length of the slot, for example by a component such as a piece of tubing placed over the drive wire between the thumb slide and the spinner. Alternatively, the handle base, thumb slide and spinner can be omitted, and drive wire proximal end 71 and sheath proximal end 51 can function as a handle, as can be seen in the lower part of FIG. 2.

FIG. 15 shows a flexible ureteroscope 120 that consists of a hand piece or body 124 and an elongate flexible shaft 121 having an outer surface 130. Shaft 121 comprises the portion of the endoscope that is inserted into the patient, while body 124 remains outside the patient. Shaft 121 consists of an articulating, deflectable, or distal portion 122 and a proximal portion 123. The outside diameter of proximal portion 123 is generally larger than the outside diameter of distal portion 122. The length of proximal portion 123 is generally greater than the length of distal portion 122. Located proximal to proximal portion 123 is body 124, which includes a working channel insertion region or port 125. The ureteroscope's working channel begins at insertion port 125 and passes through the entire length of the shaft, emerging at the distal end or exiting region 127 of distal portion 122. Other components typically used in an endoscope are not shown. Distal portion 122 can be articulated or deflected by the user by means of a control located on body 124. For typical flexible ureteroscopes, the maximum deflection is about 180 degrees.

FIG. 15a is an enlarged cross-section of distal portion 122, and shows the outside diameter 132 of surface 130 of the distal portion of the shaft. This view shows some of the elements inside the shaft, including an optical system 136 for transmitting images proximate to the distal end of the endoscope, a light guide 138, and an elongated channel or working channel 140. Other elements inside the shaft, such as deflection mechanism components for an articulating flexible endoscope, are not shown. Working channel 140 is surrounded and defined by an encasement or tubing 142, which has an inner surface 144. Encasement 142 has an inside dimension or inner diameter 146. The encasement inner surface 144 defines the working channel 140 and the inner diameter of the encasement equates to the diameter of the working channel. FIG. 16 shows specifications for several flexible ureteroscopes, all of which have a single working channel with inside diameter of 3.6 Fr. The length of the working channel, which consists of the length of the shaft plus the distance from the insertion port to the shaft, is about 80 cm for the Olympus URF/P3, for example, although working channel lengths of longer or shorter dimensions are also contemplated within the scope of the present invention.

FIG. 17 shows a longitudinal cross-sectional view of an endoscope working channel with a retrieval device according to the present invention positioned within the working channel. Working channel 140 is defined by encasement inner surface 144, and extends from insertion port 125 to exiting region 127. Working channel 140 has a proximal region 148a that corresponds to the proximal portion of the shaft, and a distal region 148b that corresponds to the distal or articulating portion of the flexible ureteroscope shaft. Throughout its length, the working channel has a generally uniform inner diameter, which for a flexible ureteroscope is 3.6 Fr. The retrieval device is positioned within working channel 140 as it would be during a retrieval procedure. Sheath 50 is positioned so that sheath proximal portion 50a is located approximately within working channel proximal region 148a, sheath intermediate portion 50b is located approximately within working channel distal region 148b, and sheath distal portion 50c is located approximately adjacent to or outside of exiting region 127. When irrigation fluid is flowing through working channel 140, sheath proximal portion 50a causes a flow resistance $R_a$ and sheath intermediate portion 50b causes a flow resistance $R_b$. At constant pressure, flow resistances $R_a$ and $R_b$ reduce the irrigation fluid flow rate through working channel 140. When the sheath diameter is generally uniform in proximal portion 50a and intermediate portion 50b, flow resistances $R_a$ and $R_b$ are approximately equal. A smaller sheath diameter results in less flow resistance, since less of the working channel is filled by the sheath, and thus a greater rate of fluid flow. If the diameter of sheath intermediate portion 50b is greater than the diameter of sheath proximal portion 50a, flow resistance $R_b$ will be greater than flow resistance $R_a$. FIG. 17a is an end view of FIG. 17, showing sheath 50 within working channel 140.

FIG. 18 is similar to FIG. 17, but shows a laser fiber 150 additionally positioned within the working channel along with a retrieval device according to the present invention. Laser fiber 150 has a proximal end 155 and a distal end 157. Laser fiber 150 passes completely through working channel 140 such that proximal end 155 is located outside insertion port 125 and distal end 157 is located beyond exiting region 127. Laser fiber 150 has a generally uniform diameter. For example, a 272 μm fiber for a holmium:yttrium-aluminum-garnet laser has an outside diameter, including cladding, of about 400 μm (1.2 Fr). When irrigation fluid is flowing through working channel 140, sheath proximal portion 50a and laser fiber 150 cause a flow resistance $R_a$ and sheath intermediate portion 50b and laser fiber 150 cause a flow resistance $R_b$. Flow resistances $R_a$ and $R_b$ are greater with the laser fiber additionally present in the working channel, because more of the working channel is filled. This results in a further reduced irrigation fluid flow rate through the working channel at constant pressure. By decreasing the sheath diameter, flow resistance is decreased and the irrigation fluid flow rate is increased. FIG. 18a is an end view of FIG. 18, showing sheath 50 and laser fiber 150 within working channel 140.

Currently marketed tipless stone baskets that can be used with flexible ureteroscopes (see Table A below) range from 1.9 Fr to 3.2 Fr.

TABLE A

U.S. Market for Ureteral Tipless Stone Baskets
Source: IMS Health, Hospital Supply Index, December 2004
Data proprietary to IMS Health

| Tipless Basket Sheath Size (Fr) | Annual Units Sold | Percent of Market |
| --- | --- | --- |
| 2.9-3.3 | 16,698 | 35% |
| 2.4-2.8 | 18,355 | 38% |
| 1.9-2.3 | 13,119 | 27% |
| 1.4-1.8 | 0 | 0 |
| 0.9-1.3 | 0 | 0 |

TABLE A-continued

U.S. Market for Ureteral Tipless Stone Baskets
Source: IMS Health, Hospital Supply Index, December 2004
Data proprietary to IMS Health

| Tipless Basket Sheath Size (Fr) | Annual Units Sold | Percent of Market |
|---|---|---|
| 0.4-0.8 | 0 | 0 |
| <0.4 | 0 | 0 |
| Total | 48,172 | 100% |

FIG. 19 shows the setup of a bench test that was performed to demonstrate the advantage of the reduced sheath diameter according to the present invention over prior art tipless stone baskets. Following is a detailed description of the test. Sterile irrigation water (Baxter 2F7114) was placed in a container elevated 136 cm (approximately 100 mm Hg pressure) above the experimental set-up. This pressure was selected because similar flow testing methods were described by Landman, et al, "Bare Naked Baskets: Ureteroscope Deflection and Flow Characteristics with Intact and Disassembled Ureteroscopic Nitinol Stone Baskets," The Journal of Urology, vol. 167, 2377-2379, June 2002. Polyurethane tubing with a stop valve was connected to the bottom of the fluid container. The free end of the tube was connected to the irrigation port of a Touhy Borst adapter. The scope working channel model (stainless steel tubing 80 cm long with 3.6 Fr inside diameter) was connected to the luer connector of the adapter. The stone basket shaft was placed through the adapter and operably engaged within the scope working channel model such that the stone basket shaft extended beyond both ends as shown in FIG. 19. Finally, the adapter was tightened down on the stone basket shaft model to seal against fluid loss. A graduated cylinder was used as a catch container to collect the fluid. Several different tipless stone baskets were tested, including three common prior art sizes: 3.0 Fr (Boston Scientific Corp. part number 390-103), 2.4 Fr (Boston Scientific Corp. part number 390-101), and 1.9 Fr (Boston Scientific Corp. part number 390-105); and four sheath diameters according to the present invention, 1.83 Fr, 1.71 Fr, 1.60 Fr and 1.52 Fr, all with uniform diameter for the entire length of the sheath.

The working channel model was tested for fluid flow rate while containing each of the different sized sheaths, as well as with the working channel empty. Additionally, for the 1.9 Fr and smaller sizes, the fluid flow rate was measured for the working channel containing both the stone basket and a laser fiber having an outer diameter of 400 µm (Laser Peripherals LLC, model number HBLF-200). The 3.0 and 2.4 Fr stone baskets were not tested with the laser fiber, because these sizes will not fit in the working channel together with the laser fiber. To begin, a small amount of fluid was run through the system to purge any trapped air. Fluid collected was returned to the elevated container. The catch container was zeroed out on a digital gram scale and then positioned below the distal end of the scope working channel model. Fluid was allowed to flow through the system for a period of time measured with a stopwatch and was collected with the catch container. The catch container was weighed and the amount of fluid was calculated assuming that 1 gram of water equals 1 ml. Data was recorded in ml/minute. The fluid was returned to the elevated container and the catch container was zeroed out again for the next trial.

The results are shown in FIG. 20. The results of this bench test demonstrate that fluid flow through a flexible uretero-scope working channel containing a stone basket shaft is significantly improved with the tipless stone basket according to the present invention, as compared with prior art tipless stone baskets, both when the stone basket is tested alone and together with a small diameter laser fiber. For example, when compared to the prior art tipless stone basket (1.9 Fr) having the best flow rate, the flow rate for a 1.71 Fr stone basket according to the present invention is increased by 46% for the stone basket alone, and 26% for the stone basket and laser fiber. For a 1.52 Fr stone basket according to the present invention, the flow rate is increased by 83% for the stone basket alone, and 72% for the stone basket and laser fiber, when compared to the prior art 1.9 Fr size. Additionally, the flow rate for a 1.52 Fr stone basket according to the present invention together with the laser fiber is similar to the flow rate for the prior art 1.9 Fr size without the laser fiber. When engaged in a 3.6 Fr working channel 80 cm long with irrigation pressures of 100 mm Hg, preferred embodiments of the present invention enable irrigation flow of generally greater than 9 ml/minute, preferably greater than 11 ml/minute, and optimally greater than 13 ml/minute. When the working channel is additionally occupied by a laser fiber having an outside diameter of approximately 400 µm, preferred embodiments of the present invention enable irrigation flow of generally greater than 4 ml/minute, preferably greater than 5 ml/minute, and optimally greater than 6 ml/minute. While the examples have discussed a laser fiber, similar benefits would be recognized for appropriately sized working elements of other devices, such as electrohydraulic or pneumatic lithotripsy devices.

In another embodiment, the medical retrieval device could be used in conjunction with a 1.9 Fr electrohydraulic lithotripsy (EHL) probe, as is offered by ACMI Corporation (part number E4-2F). An advantage of EHL probes over laser fibers is that EHL probes enable greater endoscope deflection because they are more flexible than laser fibers. Also, EHL probes can be passed through a fully deflected flexible ureteroscope, whereas this cannot typically be done with holmium laser fibers. In this embodiment, the shaft or sheath outer diameter or its average would generally be less than 1.7 Fr, preferably less than 1.6 Fr, and optimally less than 0.1.5 Fr. Sizes of 1.7 Fr or greater will not fit together with a 1.9 Fr EHL probe in a 3.6 Fr working channel. Outside diameter 57 or its average is generally greater than 0.4 Fr, preferably greater than 0.8 Fr, and optimally greater than 1.1 Fr.

Another embodiment of the present invention is a stone retrieval system for use within a working channel of a flexible endoscope, the working channel having an inner diameter of less than 3.7 Fr. The stone retrieval system comprises a lithotripsy device and a medical retrieval device as described herein, both adapted to be inserted into the working channel of the flexible endoscope, and a source of irrigation fluid fluidly coupled to the endoscope to introduce irrigation fluid into the proximal portion of the working channel at an irrigation flow rate. In this embodiment, the irrigation flow rate exiting the distal portion of the working channel is sufficient for stone visualization when both the lithotripsy device and the medical retrieval device are simultaneously positioned in the working channel.

It can be seen that the retrieval device according to one embodiment of the present invention provides significantly improved irrigation fluid flow rates as compared to prior art tipless stone baskets. This results in greater visibility in the field of view, facilitating rapid stone retrieval and potentially improving stone retrieval success rates.

It can also be seen that one embodiment of the present invention provides a sheath for a retrieval device that can be used along side a second device, such as a laser fiber, within in a single working channel and still allow for sufficient irrigation flow. This reduces the need for multiple exchanges of retrieval and lithotripsy devices during a procedure. This decreased handling reduces the likelihood of damage to the delicate instruments, and can shorten the procedure. The present invention also provides a safety feature. In the event that a stone too large to remove intact cannot be released from the basket, the small diameter of the sheath leaves sufficient space in the working channel to allow passage of a laser fiber along side the sheath to fragment the entrapped stone.

It can also be seen that the retrieval device according to one embodiment of the present invention provides a shaft that varies in flexibility to match the capability of a flexible ureteroscope and to avoid limiting the deflection of the flexible ureteroscope.

It will be appreciated that one embodiment of the present invention is particularly well suited for a tipless stone basket used to retrieve stones located in a calyx of the kidney.

Another aspect of the invention is the method of manufacturing the medical retrieval device as described above.

Another embodiment of the present invention is a method for operating a plurality of devices and an endoscope to manipulate a stone in a patient. The endoscope includes a working channel having an inner diameter less than 3.7 Fr and an optical system for transmitting images proximate a distal end of the endoscope. The method comprises inserting a first device into the working channel of the endoscope, inserting a second device into the working channel while the first device is in the working channel, and positioning the second device longitudinally adjacent to the first device. At least one of the first and second devices is utilized to manipulate the stone in the patient while the first device and the second device are both in the working channel. Irrigation through the working channel while the first and second devices are both in the working channel is such that an effective irrigation flow rate is achieved to maintain visualization of the stone via the optical system of the endoscope. In one embodiment, the step of irrigating is performed such that the effective irrigation flow rate is at least 9 ml/minute when normalized to a working channel having an inner diameter of 3.6 Fr and a length of 80 cm at an irrigation fluid pressure of 100 mm Hg. In one embodiment, the step of inserting the first device is accomplished by inserting a medical retrieval device having a substantially tipless basket and a shaft that has an average outer diameter of less than 1.9 Fr. In one embodiment, the step of inserting the second device is accomplished by inserting a device selected from a group consisting of: a laser fiber, an EHL probe, a guide wire, a catheter, a stylet, an endoscopic grasping device, and a lithotripsy device, or any combination thereof.

While in preferred embodiments the present invention relates to retrieving stones or calculi from the urinary system using a ureteroscope, several other applications are envisioned as well. For example, the retrieval of biliary stones, gall bladder stones, or other objects or tissue during the course of an endoscopic or laparoscopic procedure. The present invention may be embodied in other specific forms without departing from the spirit or essential attributes thereof, and it is therefore desired that the present embodiments be considered in all respects as illustrative and not restrictive.

What is claimed is:

1. A medical device for use in a procedure for entrapping an object, the device comprising:
   a sheath;
   a basket formed of a plurality of flexible elements having:
      a closed configuration when said flexible elements are retracted within said sheath, and
      an open configuration when said flexible elements are extended from said sheath such that said basket defines an entrapment space for entrapping said object, said entrapment space including a proximal end nearest the sheath and a distal end,
      wherein at least one of said plurality of flexible elements presents an inner surface facing said entrapment space, the inner surface having a width at said distal end of said entrapment space that is wider than a width at said proximal end of said entrapment space; and
   a drive wire connected to said basket, said drive wire and said sheath being moveable relative to one another to effect opening and closing of said basket,
   wherein said sheath has an average outside diameter of less than 1.9 Fr.

2. The medical device of claim 1 wherein said sheath has an average outside diameter of less than 1.7 Fr.

3. The medical device of claim 1 wherein said flexible elements are joined with an additional component at the distal end of said entrapment space to provide a substantially tipless configuration.

4. The medical retrieval device of claim 1 wherein said object is a kidney stone.

5. The medical retrieval device of claim 1 wherein at least two of said flexible elements having a plurality of cross sectional shapes along a longitudinal portion of said flexible elements, and at least one of said cross sectional shapes being generally uniform and non-round.

6. The medical device of claim 1 wherein said sheath has an average outside diameter of less than 1.7 Fr and said flexible elements are joined with an additional component at the distal end of said entrapment space to provide a substantially tipless configuration and said object is a kidney stone.

7. The medical device of claim 1, wherein said sheath is moveable over said drive wire to effect opening and closing of said basket.

8. A medical device for use in a procedure for entrapping an object, the device comprising:
   a sheath having an outside diameter and a proximal end and a distal end and defining a lumen there between;
   a basket formed of a plurality of flexible elements having:
      an open configuration when said basket is extended from said sheath such that said basket defines an entrapment space for entrapping said object and having a corresponding open basket diameter, and,
      a closed configuration when said basket is retracted within said sheath such that a portion of said flexible elements remain outside of said sheath, said outside portion of said flexible elements having a corresponding closed diameter that still defines a retention space wherein said retention space is smaller than said entrapment space and wherein said outside portion of said flexible elements being prevented by size from entering said sheath lumen;
   a drive wire connected to said basket, said drive wire and said sheath being moveable relative to one another to effect opening and closing of said basket,
   wherein said closed diameter is greater than said sheath diameter and said sheath diameter is less than 1.9 Fr.

9. The medical device of claim 8 wherein said sheath has an average outside diameter of less than 1.7 Fr.

10. The medical device of claim 8 wherein said flexible elements are joined with an additional component at the distal end of said basket to provide a substantially tipless configuration.

11. The medical retrieval device of claim 8 wherein said object is a kidney stone.

12. The medical retrieval device of claim 8 wherein at least two of said flexible elements having a plurality of cross sectional shapes along a longitudinal portion of said flexible elements.

13. The medical device of claim 8 wherein said sheath has an average outside diameter of less than 1.7 Fr and said flexible elements are joined with an additional component at the distal end of said basket to provide a substantially tipless configuration and said object is a kidney stone.

14. The medical device of claim 8, wherein said sheath is moveable over said drive wire to effect opening and closing of said basket.

15. The medical device of claim 8, further comprising a handle having stops to effect said open configuration and said closed configuration of said basket, said stops configured to limit the movement of said drive wire and said sheath relative to one another.

16. A medical device for use in a procedure for entrapping an object, the device comprising:
 a sheath;
 a basket formed of a plurality of flexible elements having:
  a closed configuration when said basket is retracted within said sheath, and
  an open configuration when said basket is extended from said sheath such that said basket defines an entrapment space for entrapping a stone,
  at least one of said flexible elements having a width at a distal end of the entrapment space that is wider than a width at a proximal end of the entrapment space, the proximal end nearest said sheath, and,
 a drive wire connected to said basket, said drive wire and said sheath moveable relative to one another to effect opening and closing of said basket,
 wherein said sheath has an average outside diameter of less than 1.9 Fr.

17. The medical device of claim 16 wherein said sheath has an average outside diameter of less than 1.7 Fr.

18. The medical device of claim 16 wherein said flexible elements are joined with an additional component at the distal end of said basket to provide a substantially tipless configuration.

19. The medical retrieval device of claim 16 wherein said object is a kidney stone.

20. The medical device of claim 16 wherein said closed configuration when said basket is retracted within said sheath has a portion of said flexible elements remaining outside of said sheath, said closed configuration outside portion having a corresponding closed diameter where said flexible elements are most outwardly disposed and said closed diameter is greater than said sheath diameter and said sheath diameter on average is less than 1.9 Fr.

21. The medical device of claim 16 wherein said sheath has an average outside diameter of less than 1.7 Fr and said flexible elements are joined with an additional component at the distal end of said basket to provide a substantially tipless configuration and said object is a kidney stone.

22. The medical device of claim 16, wherein at least one of said flexible elements includes a plurality of cross sectional shapes along a longitudinal portion of said flexible element.

23. The medical device of claim 22, wherein at least one of said cross sectional shapes is generally uniform and non-round.

24. The medical device of claim 16, wherein said sheath is moveable over said drive wire to effect opening and closing of said basket.

\* \* \* \* \*